US012594156B2

(12) United States Patent
Tang et al.

(10) Patent No.: US 12,594,156 B2
(45) Date of Patent: Apr. 7, 2026

(54) PROSTHESIS FOR THE LUNG AND THE USE THEREOF

(71) Applicant: National Institute of Biological Sciences, Beijing, Beijing (CN)

(72) Inventors: Nan Tang, Beijing (CN); Huijuan Wu, Beijing (CN); Jiao Li, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 1081 days.

(21) Appl. No.: 17/614,768

(22) PCT Filed: May 30, 2019

(86) PCT No.: PCT/CN2019/089356
§ 371 (c)(1),
(2) Date: Nov. 29, 2021

(87) PCT Pub. No.: WO2020/237586
PCT Pub. Date: Dec. 3, 2020

(65) Prior Publication Data
US 2022/0273413 A1 Sep. 1, 2022

(51) Int. Cl.
*A61F 2/04* (2013.01)

(52) U.S. Cl.
CPC .......... *A61F 2/04* (2013.01); *A61F 2002/043* (2013.01); *A61F 2230/0013* (2013.01); *A61F 2230/0015* (2013.01)

(58) Field of Classification Search
CPC .................. A61F 2/04; A61F 2002/043; A61F 2230/0013; A61F 2230/0015; A61F 2220/0008
See application file for complete search history.

(56) References Cited

U.S. PATENT DOCUMENTS

| | | | |
|---|---|---|---|
| 6,514,290 B1 | 2/2003 | Loomas | |
| 6,653,525 B2 | 11/2003 | Ingenito et al. | |
| 9,610,150 B2 * | 4/2017 | Flanagan | A61F 2/04 |
| 10,258,457 B1 | 4/2019 | Jweied et al. | |
| 2009/0255537 A1 | 10/2009 | Shaw et al. | |
| 2012/0010636 A1 | 1/2012 | Boey et al. | |
| 2012/0141439 A1 | 6/2012 | Ott | |
| 2015/0265392 A1 | 9/2015 | Flanagan et al. | |
| 2015/0272591 A1 * | 10/2015 | Folan | A61B 17/12136 606/191 |

(Continued)

FOREIGN PATENT DOCUMENTS

| | | |
|---|---|---|
| CN | 101172063 A | 5/2008 |
| CN | 105232180 A | 1/2016 |

(Continued)

OTHER PUBLICATIONS

Ding L, et al., "Bone Marrow CD11c+ Cell-Derived Amphiregulin Promotes Pulmonary Fibrosis", Journal of Immunology, vol. 197, No. 1, Jul. 1, 2016, pp. 303-312.

(Continued)

*Primary Examiner* — Bruce E Snow
(74) *Attorney, Agent, or Firm* — Duane Morris LLP

(57) ABSTRACT

The invention relates to prosthesis for treating pulmonary fibrosis, in particular, idiopathic pulmonary fibrosis (IPF), and a method for treating pulmonary fibrosis, in particular, idiopathic pulmonary fibrosis (IPF).

16 Claims, 16 Drawing Sheets
Specification includes a Sequence Listing.

(56)                References Cited

U.S. PATENT DOCUMENTS

| | | | |
|---|---|---|---|
| 2016/0228495 | A1 | 8/2016 | Weihua |
| 2017/0049554 | A1 | 2/2017 | Li et al. |
| 2018/0325525 | A1 | 11/2018 | Veeckmans et al. |
| 2019/0192163 | A1 | 6/2019 | Vasquez et al. |
| 2020/0026060 | A1 | 1/2020 | Takato |

FOREIGN PATENT DOCUMENTS

| | | | |
|---|---|---|---|
| WO | 2009015233 | A2 | 1/2009 |
| WO | 2010093333 | A1 | 8/2010 |
| WO | 2010128464 | A1 | 11/2010 |
| WO | 2010137012 | A1 | 12/2010 |
| WO | 2014151557 | A2 | 9/2014 |
| WO | 2015168387 | A2 | 11/2015 |
| WO | 2018203465 | A1 | 11/2018 |
| WO | 2018217849 | A1 | 11/2018 |

OTHER PUBLICATIONS

Stolarczyk M. et al., "The EGFR-ADAM17 Axis in Chronic Obstructive Pulmonary Disease and Cystic Fibrosis Lung Pathology", Mediators of Inflammation, vol. 2018, Jan. 19, 2018, pp. 1-22.

Wynn, T. A. Cellular and molecular mechanisms of fibrosis. The Journal of pathology 214, 199-210, doi: 10.1002/path.2277 (2008).

Wynn, T. A. & Ramalingam, T. R. Mechanisms of fibrosis: therapeutic translation for fibrotic disease. Nature medicine 18, 1028-1040, doi:10.1038/nm.2807 (2012).

Mehal, W. Z., Iredale, J. & Friedman, S. L. Scraping fibrosis: expressway to the core of fibrosis. Nature medicine 17, 552-553, doi:10.1038/nm0511-552 (2011).

Barkauskas, C. E. & Noble, P. W. Cellular mechanisms of tissue fibrosis. 7. New insights into the cellular mechanisms of pulmonary fibrosis. American journal of physiology. Cell physiology 306, C987-996, doi:10.1152/ajpcell.00321.2013 (2014).

Rock, J. R. et al. Multiple stromal populations contribute to pulmonary fibrosis without evidence for epithelial to mesenchymal transition. Proceedings of the National Academy of Sciences of the United States of America 108, E1475-1483, doi:10.1073/pnas.1117988108 (2011).

Gross, T. J. & Hunninghake, G. W. Idiopathic pulmonary fibrosis. New England Journal of Medicine 345, 517-525 (2001).

Vyalov, S. L., Gabbiani, G. & Kapanci, Y. Rat alveolar myofibroblasts acquire alpha-smooth muscle actin expression during bleomycin-induced pulmonary fibrosis. The American journal of pathology 143, 1754 (1993).

King Jr, T. E., Pardo, A. & Selman, M. Idiopathic pulmonary fibrosis. The Lancet 378, 1949-1961 (2011).

Plantier, L. et al. Ectopic respiratory epithelial cell differentiation in bronchiolised distal airspaces in idiopathic pulmonary fibrosis. Thorax 66, 651-657, doi:10.1136/thx.2010.151555 (2011).

Steele, M. P. & Schwartz, D. A. Molecular mechanisms in progressive idiopathic pulmonary fibrosis. Annual review of medicine 64, 265-276, doi:10.1146/annurev-med-042711-142004 (2013).

Camelo, A., Dunmore, R., Sleeman, M. A. & Clarke, D. L. The epithelium in idiopathic pulmonary fibrosis: breaking the barrier. Frontiers in pharmacology 4, 173, doi:10.3389/fphar.2013.00173 (2014).

Barkauskas, C. E. et al. Type 2 alveolar cells are stem cells in adult lung. The Journal of clinical investigation 123, 3025-3036, doi:10.1172/JCI68782 (2013).

Desai, T. J., Brownfield, D. G. & Krasnow, M. A. Alveolar progenitor and stem cells in lung development, renewal and cancer. Nature 507, 190-194, doi:10.1038/nature 12930 (2014).

Haies, D. M., Gil, J. & Weibel, E. R. Morphometric study of rat lung cells: I. Numerical and dimensional characteristics of parenchymal cell population. American Review of Respiratory Disease 123, 533-541 (1981).

Selman, M. & Pardo, A. Idiopathic pulmonary fibrosis: an epithelial/fibroblastic cross-talk disorder. Respiratory research 3, 3 (2001).

Kropski, J. A., Blackwell, T. S. & Loyd, J. E. The genetic basis of idiopathic pulmonary fibrosis. European Respiratory Journal 45, 1717-1727 (2015).

Goodwin, A. T. & Jenkins, G. Molecular endotyping of pulmonary fibrosis. Chest 149, 228-237 (2016).

Xu, Y. et al. Single-cell RNA sequencing identifies diverse roles of epithelial cells in idiopathic pulmonary fibrosis. JCI insight 1 (2016).

Sternlicht, M. D. & Sunnarborg, S. W. The ADAM17-amphiregulin-EGFR axis in mammary development and cancer. Journal of mammary gland biology and neoplasia 13, 181-194 (2008).

Berasain, C. & Avila, M. A. in Seminars in cell & developmental biology. 31-41 (Elsevier).

Sternlicht, M. D. et al. Mammary ductal morphogenesis requires paracrine activation of stromal EGFR via ADAM17-dependent shedding of epithelial amphiregulin. Development 132, 3923-3933 (2005).

Macias, H. & Hinck, L. Mammary gland development. Wiley Interdisciplinary Reviews: Developmental Biology 1, 533-557 (2012).

Busser, B., Sancey, L., Brambilla, E., Coll, J.-L. & Hurbin, A. The multiple roles of amphiregulin in human cancer. Biochimica et Biophysica Acta (BBA)-Reviews on Cancer 1816, 119-131 (2011).

Chen, Z. et al. Aberrantly activated AREG-EGFR signaling is required for the growth and survival of CRTC1-MAML2 fusion-positive mucoepidermoid carcinoma cells. Oncogene 33, 3869 (2014).

Busser, B. et al. Amphiregulin promotes resistance to gefitinib in nonsmall cell lung cancer cells by regulating Ku70 acetylation. Molecular Therapy 18, 536-543 (2010).

Wang, X., Masri, S., Phung, S. & Chen, S. The role of amphiregulin in exemestane-resistant breast cancer cells: evidence of an autocrine loop. Cancer research 68, 2259-2265 (2008).

Zhou, Y. et al. Amphiregulin, an epidermal growth factor receptor ligand, plays an essential role in the pathogenesis of transforming growth factor-$\beta$-induced pulmonary fibrosis. Journal of Biological Chemistry 287, 41991-42000 (2012).

Chen, L. et al. Cdc42 deficiency causes Sonic hedgehog-independent holoprosencephaly. Proceedings of the National Academy of Sciences 103, 16520-16525 (2006).

Council, N. R. Guide for the care and use of laboratory animals. (National Academies Press, 2010).

Foltz, C. J. & Ullman-Cullere, M. Guidelines for assessing the health and condition of mice. Resource 28 (1999).

Luetteke, N. C. et al. Targeted inactivation of the EGF and amphiregulin genes reveals distinct roles for EGF receptor ligands in mouse mammary gland development. Development 126, 2739-2750 (1999).

Wang, Y. et al. Pulmonary alveolar type I cell population consists of two distinct subtypes that differ in cell fate. Proceedings of the National Academy of Sciences, 201719474 (2018).

Lynch, D. A. et al. Diagnostic criteria for idiopathic pulmonary fibrosis: a Fleischner Society White Paper. The Lancet Respiratory Medicine 6, 138-153, doi:10.1016/s2213-2600(17)30433-2 (2018).

Nogee, L. M. et al. A mutation in the surfactant protein C gene associated with familial interstitial lung disease. New England Journal of Medicine 344, 573-579 (2001).

Seibold, M. A. et al. A common MUC5B promoter polymorphism and pulmonary fibrosis. New England Journal of Medicine 364, 1503-1512 (2011).

Wang, Y. et al. Genetic defects in surfactant protein A2 are associated with pulmonary fibrosis and lung cancer. The American Journal of Human Genetics 84, 52-59 (2009).

Meltzer, E. B. & Noble, P. W. Idiopathic pulmonary fibrosis. Orphanet journal of rare diseases 3, 8, doi:10.1186/1750-1172-3-8 (2008).

Richeldi, L., Collard, H. R. & Jones, M. G. Idiopathic pulmonary fibrosis. The Lancet 389, 1941-1952, doi:10.1016/s0140-6736(17)30866-8 (2017).

King et al.—AmericanThoracicSociety, Idiopathic pulmonary fibrosis. American journal of respiratory and critical care medicine 161, 646-664 (2000).

(56) References Cited

OTHER PUBLICATIONS

Lynch, D. A. et al. High-resolution computed tomography in idiopathic pulmonary fibrosis: diagnosis and prognosis. American journal of respiratory and critical care medicine 172, 488-493 (2005).

Noble, P. W. et al. Pirfenidone in patients with idiopathic pulmonary fibrosis (CAPACITY): two randomised trials. The Lancet 377, 1760-1769 (2011).

Raghu, G. et al. An official ATS/ERS/JRS/ALAT statement: idiopathic pulmonary fibrosis: evidence-based guidelines for diagnosis and management. American journal of respiratory and critical care medicine 183, 788-824 (2011).

Japanese Patent Office, Japanese Notice of Reasons for Refusal and Search Report issued for corresponding Japanese Patent Application No. 2021-571453 on Dec. 27, 2022 (English translation provided).

Reconsideration Report by Examiner before Appeal from JPO, Nov. 19, 2024, 2 pages.

Japanese Patent Office, Notice of Transfer of a Case for Reconsideration by Examiners before Appeal Proceedings, Oct. 4, 2024, 2 pages.

Japanese Patent Office, Notice of Termination of Reconsideration by Examiners before Appeal Proceedings, Nov. 22, 2024, 2 pages.

Notice of Non-Final Rejection from KIPO, Jul. 24, 2024, 32 pages.

Notice of Allowance from IP Canada, May 29, 2023, 1 page.

Notice of Acceptance from IP Australia, Mar. 23, 2023, 4 pages.

Korean Request for the Submission of an Opinion. Oct. 19, 2023, 6 pages.

Japanese Written Opinion, Apr. 10, 2023, 6 pages.

Japanese Notice of Reasons for Refusal-20230718, 10 pages.

Japanese Notice of Reasons for Refusal-20221227, 4 pages.

European Search Opinion & Supplementary European Search Report, May 16, 2023, 5 pages.

Decision of Rejection from JPO, Mar. 4, 2024, 6 pages.

Canadian Intellectual Property Office, First Office Action issued on Jun. 9, 2022, for corresponding Canadian Patent Application No. 3,141,912.

IP Australia (Australian Patent Office), First Office Action issued on Sep. 13, 2022, for corresponding Australian Patent Application No. 2019448791.

Request for Submission of an Opinion dated Apr. 27, 2025 for corresponding application No. 10-2021-7042760 from the Korean Intellectual Property Office.

* cited by examiner 1A  1B  1C 1D  1E  1F 2A  2B 2C  2D

The *Cdc42* sequence before deleting the exon2 of the *Cdc42* gene:

5'TGTTCTATTTTAAAGTACAGGTAATCATGCATGAGAAGTCAAAACCTTTAAAACTGTCAAACAGTGGGCTGC
TGTGTGTGGCATTTGCTGCCAACCATGACAACCTAAGTTCAACTTAAGAGCCCAACAATGGAAAAAGACCCCT
TCAAGTTGTCCTCTGCCATCTACACATACACCAAAGCAGGACACAGGTATGTACAGAATTCATAACTTCGTATA
ATGTATGCTATACGAAGTTAT<u>GTTCGAACGAAGTTCCTATTCTCTAGAAAGTATAGGAACTTCGCTAGACTAGTACG</u>
<u>CGTGTACACCTTGTAATTGCTGCTCTGAGCAAGTTGCCATTTTTTCTTTTTAGAGGTTTTCAGTCATAGCAGTAATGCT</u>
<u>AGTTCTGGTTTGAGTGGCTGAGCCCTGTTGCTAGGGGAAAAAAGTATGGATTTAAACATAAATCAATAAAATAATTGTC</u>
<u>TTTAATTCTTCTTAGGACAAGATCTAATTTGAAATATTAAAAGTGGATACAAAACTGTTTCCGAAATGCAGACAATTA</u>
<u>AGTGTGTTGTTGTTGGTGATGGTGCTGTTGGTAAAACATGTCTCCTGATATCCTACACAACAAACAAATTCCCATCGG</u>
<u>AATATGTACCAACTGTAAGTATAAAAGGCTTTTTACTAGCAAAAGATTGTAATGTAGTGTCTGTCCATTGGAAAACACTT</u>
<u>GGCCTGCCTGCAGTATTTTTGACTGTCTTGCCCTTTAAAAAAAAATTAAATTTTACTACCTTTATTACTTTGTGGGTGT</u>
<u>GTGTT</u>ATAACTTCGTATAATGTATGCTATACGAAGTTATGGTACCGAATTCAGTTTCTGGACCTTGTTGTTTTGT
CTTAAGTATCAAAGTAGAACAGTGACCGATATATTCCTTTTATTTTTTTTTTTCTTCCCTGAGACTGGGTTTCTC
TGTGTAGCCCTTGCTGTTCTGTAACTCACTCTGTGAGTGGCCTCAAACTCAGAGATCCGCCTGCCTTGGGCA
AGGAAGGTGCTATAAAAAGAGTCTCGTGTGGTATATGAAGTATAGTTTGTGAAAGCTGCTTCAGTGTGAGCAC
ACACGCATTATATGCAAGACCAATTGCAGCCCGAAGAATACTCTAAAAAATGACTCACTGCCCAG3' (SEQ ID
NO:3)

The *Cdc42* sequence after deleting the exon2 of the *Cdc42* gene:

5'TGTTCTATTTTAAAGTACAGGTAATCATGCATGAGAAGTCAAAACCTTTAAAACTGTCAAACAGTGGGCTGC
TGTGTGTGGCATTTGCTGCCAACCATGACAACCTAAGTTCAACTTAAGAGCCCAACAATGGAAAAAGACCCCT
TCAAGTTGTCCTCTGCCATCTACACATACACCAAAGCAGGACACAGGTATGTACAGAATTCATAACTTCGTATA
ATGTATGCTATACGAAGTTATGGTACCGAATTCAGTTTCTGGACCTTGTTGTTTGTCTTAAGTATCAAAGTAG
AACAGTGACCGATATATTCCTTTTATTTTTTTTTTTCTTCCCTGAGACTGGGTTTCTCTGTGTAGCCCTTGCTG
TTCTGTAACTCACTCTGTGAGTGGCCTCAAACTCAGAGATCCGCCTGCCTTGGGCAAGGAAGGTGCTATAAA
AAGAGTCTCGTGTGGTATATGAAGTATAGTTTGTGAAAGCTGCTTCAGTGTGAGCACACACGCATTATATGCA
AGACCAATTGCAGCCCGAAGAATACTCTAAAAAATGACTCACTGCCCAG3' (SEQ ID NO:4)

PROSTHESIS FOR THE LUNG AND THE USE THEREOF

PRIORITY CLAIM AND CROSS-REFERENCE

The present application is a National Stage Application, filed under 35 U.S.C. 371, of International Patent Application No. PCT/CN2019/089356, filed on May 30, 2019, which is incorporated herein by reference in its entirety.

SEQUENCE LISTING

This application contains a Sequence Listing, which is submitted electronically via EFS-Web in ASCII format with a file name H5292-00003-SEQTXT, creation date of Mar. 3, 2022, and a size of 8 kB. This sequence listing submitted is part of the specification and is herein incorporated by reference in its entirety.

INTRODUCTION

Fibrosis—the thickening and scarring of connective tissue that can result from injury—is characterized by the accumulation of extracellular matrix (ECM) components and the excessive proliferation of fibroblast cells. This disorder, which is commonly observed in organs including lungs, livers, and kidneys, among many others, causes disrupted tissue architecture and leads to major impairments in organ function[1-2]. Indeed, fibrosis can develop in nearly every organ and is a major cause of end-stage organ failure and death in a large variety of chronic diseases[3]. A common feature of pulmonary fibrosis is the excessive proliferation of fibroblasts around the air sacs of lungs (alveoli)[4]. Extensive biomedical studies have established that an increased number of fibroblasts, in combination with their excessive deposition in the ECM ultimately cause alveolar structure destruction, decreased lung compliance, and disrupted gas exchange function[5-7].

The most common type of pulmonary fibrosis is idiopathic pulmonary fibrosis (IPF). This disorder eventually affects entire lung lobes, but it begins with microscopic fibrotic lesions that occur at the peripheral regions and slowly progress inward, and this fibrosis can ultimately lead to respiratory failure[8,9]. IPF is a fatal disease with the median survival time of only 2-4 years from diagnosis[10]. Scientifically, the mechanisms and nature of the pathological progression of IPF are not fully understood, although multiple studies have implicated contributions from a specific subset of alveolar epithelial cells-alveolar type II (AT2) cells[11-13].

The alveolar epithelia of lungs are composed of a combination of both alveolar type I (AT1) and type II (AT2) cells. AT2 cells are the alveolar stem cells, and can differentiate into AT1 cells during alveolar homeostasis and post-injury repair[14,15]. AT1 cells—which ultimately constitute fully 95% of the alveolar surface in adult lungs—are large squamous cells that function as the epithelial component of the thin air-blood barrier[16]. In IPF tissues, abnormal hyperplastic AT2 cells are typically located adjacent to fibroblastic foci[17], and the gene mutants that affect the functions of AT2 cells are frequently observed in IPF tissues in the clinic[11-13,18,19]. Previously, balloon prosthesis was used to occupy the pleural cavity in order to correct tracheal shift and overdistension of the remaining lung following pneumonectomy (PNX), and such balloon is preferably constructed approximately 10% larger than the pleural cavity it is intended to occupy at the end of a normal exhalation.

Although mechanical tension is an important regulator of lung formation, function, and metabolism, studies at the cellular and molecular levels have been limited by lacking suitable tools to study the functions of mechanical tension on cells in vitro or in vivo.

SUMMARY OF THE INVENTION

The invention relates to a method for treating pulmonary fibrosis, in particular, idiopathic pulmonary fibrosis (IPF), and prosthesis for treating pulmonary fibrosis, in particular, idiopathic pulmonary fibrosis (IPF). The present invention is based on an essential regulatory role of mechanical tension in driving the development of lung fibrosis. The implanted prosthesis may reduce the level of mechanical tension on the alveolar epithelium, and rescue the enlarged alveoli phenotype. In particular, progressive lung fibrosis can be prevented by reducing the level of mechanical tension on the alveolar epithelium.

In the first place, the invention provides prosthesis for treating pulmonary fibrosis, in particular, idiopathic pulmonary fibrosis (IPF).

The prosthesis in the present invention may be designed to be placed under the pulmonary lobe, as long as at the end of normal inspiratory, the level of mechanical tension on the alveolar epithelium is reduced.

Preferably, the prosthesis is designed to be anchored under the lobes and above the diaphragm, and preferably, is designed to match with the bottom of the lobes, as long as the mechanical tension on the alveolar epithelium is reduced at the end of normal inspiratory.

Therefore, the prosthesis is surrounded by pleural fluid. Preferably, the prosthesis will occupy at least ⅛ of the space surrounded by the bottom of the lobes, diaphragm and the wall of pleural cavity at the end of normal inspiratory. Preferably, the prosthesis will occupy at least ¼ of the space surrounded by the basal of the lobes, diaphragm and the wall of pleural cavity at the end of normal inspiratory. Preferably, the prosthesis will occupy at least half of the space surrounded by the basal of the lobes, diaphragm and the wall of pleural cavity at the end of normal inspiratory. Preferably, the prosthesis will occupy at least ¾ of the space surrounded by the basal of the lobes, diaphragm and the wall of pleural cavity at the end of normal inspiratory. Preferably, the prosthesis will occupy the whole space surrounded by the basal of the lobes, diaphragm and the wall of pleural cavity at the end of normal inspiratory.

Therefore, the prosthesis is surrounded by pleural fluid. Preferably, the area of the prosthesis projected to the bottom of the lower lung lobe will account for at least ⅛ of the area of the bottom of the lower lung lobe. Preferably, the area of the prosthesis projected to the bottom of the lower lung lobe will account for at least ¼ of the area of the bottom of the lower lung lobe. Preferably, the area of the prosthesis projected to the bottom of the lower lung lobe will account for at least half of the area of the bottom of the lower lung lobe. Preferably, the area of the prosthesis projected to the bottom of the lower lung lobe will occupy at least ¾ of the area of the bottom of the lower lung lobe. Preferably, the area of the prosthesis projected to the bottom of the lower lung lobe will account for the whole area of the bottom of the lower lung lobe.

The prosthesis in the present invention comprises a body having an upper side, a lower side and a lateral side extending between the upper side and the lower side. The prosthesis upper side is preferably matched with the bottom of the lobes. The prosthesis lower side is preferably matched with the diaphragm. The prosthesis outer lateral side is preferably matched with the wall of pleural cavity between the bottom of the lobes and the diaphragm far from the heart. The prosthesis inner lateral side is preferably matched with the outer wall of the lower lung lobe. The prosthesis may be in a shape of plate, ellipse, irregular U, arc, conical, scapula, or irregular, and so on, so as to occupy the space under the lung lobes. The prosthesis has a smooth curved profile without edges and corners so as to reduce the discomfort and avoid injury to the pleura.

Alternatively, the prosthesis in the present invention comprises a body having an upper side, a lower side, a lateral side extending between the upper side and the lower side, and a medial border approaching the heart, wherein the lateral side is opposite to the medial border. The prosthesis upper side is preferably matched with the bottom of the lobes. The prosthesis lower side is preferably matched with the diaphragm. The prosthesis outer lateral side is preferably matched with the wall of pleural cavity between the bottom of the lobes and the diaphragm far from the heart. The prosthesis is in a shape of plate, ellipse, irregular U, arc, conical, scapula, or irregular, and so on, so as to occupy the space under the lower lung lobes. Preferably, the prosthesis upper side tapers toward the medial border. The prosthesis lower side tapers toward the medial border. The prosthesis has a smooth curved profile without edges and corners so as to reduce the discomfort and avoid injury to the pleura.

Preferably, the lateral side is at a height of 0.5 cm-8 cm. Preferably, the lateral side is at a height of 0.5 cm, 0.6 cm, 0.7 cm, 0.8 cm, 0.8 cm, 0.9 cm, 1 cm, 2 cm, 3 cm, 4 cm, 5 cm, 6 cm, 7 cm, or 8 cm.

Preferably, the thickness of the wall of the prosthesis is between 0.1-4 cm. Preferably, the thickness is 0.1 cm, 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 3 cm, or 4 cm.

Preferably, the prosthesis in the present invention is in a shape of arc, wherein the arc is matched with the lower edge of the lower lung lobe. Preferably, the arch is matched with at least ⅛ of the lower edge of the lower lung lobe far from the heart. Preferably, the arch is matched with at least ¼ of the lower edge of the lower lung lobe far from the heart. Preferably, the arch is matched with at least ½ of the lower edge of the lower lung lobe far from the heart. Preferably, the arch is matched with the overall length of the lower edge of the lower lung lobe.

Preferably, the prosthesis is at a height of 1 cm-4 cm. Preferably, the lateral side is at a height of 1 cm, 2 cm, 3 cm, or 4 cm.

Preferably, the prosthesis is designed to be placed in the pleural cavity, in particular, the prosthesis is placed at the lower side of the pleural cavity, so as to reduce the mechanical tension on the alveolar epithelium at the end of normal inspiratory. The prosthesis may be fixed in the pleural cavity, in particular, the prosthesis is placed at the lower side of the pleural cavity. For example, the prosthesis may be sutured to the pleural cavity wall using surgical sutures, particularly, the lower portion of the pleural cavity wall. Preferably, the prosthesis is sutured to of the wall of pleural cavity through the pinholes on the lateral side.

The prosthesis may be made of soft spongy latex, foam latex, 380 micron hollow fiber, gelatin foam, material, plastic sponge (Ivalon), polythene bag filled with fiberglass, rubber, silicone rubber, silicone gel, carbon materials involving carbon nanotube, grapheme, ultra-light porous carbon, hollow porous carbon, carbon fiber, carbon titanium alloy, and et., al.

The prosthesis may be solid, or the prosthesis may be a pocket or a sack, filled with fluid or jelly.

In the second place, the invention provides use of prosthesis for treating pulmonary fibrosis, in particular, idiopathic pulmonary fibrosis (IPF).

The prosthesis in the present invention may be designed to be placed under the pulmonary lobe, as long as at the end of normal inspiratory, the level of mechanical tension on the alveolar epithelium is reduced.

Preferably, the prosthesis is designed to be anchored under the lobes and above the diaphragm, and preferably, is designed to match with the bottom of the lobes, as long as the mechanical tension on the alveolar epithelium is reduced at the end of normal inspiratory.

Therefore, the prosthesis is surrounded by pleural fluid. Preferably, the prosthesis will occupy at least ⅛ of the space surrounded by the bottom of the lobes, diaphragm and the wall of pleural cavity at the end of normal inspiratory. Preferably, the prosthesis will occupy at least ¼ of the space surrounded by the bottom of the lobes, diaphragm and the wall of pleural cavity at the end of normal inspiratory. Preferably, the prosthesis will occupy at least half of the space surrounded by the bottom of the lobes, diaphragm and the wall of pleural cavity at the end of normal inspiratory. Preferably, the prosthesis will occupy at least ¾ of the space surrounded by the bottom of the lobes, diaphragm and the wall of pleural cavity at the end of normal inspiratory. Preferably, the prosthesis will occupy the whole space surrounded by the bottom of the lobes, diaphragm and the wall of pleural cavity at the end of normal inspiratory.

Therefore, the prosthesis is surrounded by pleural fluid. Preferably, the area of the prosthesis projected to the bottom of the lower lung lobe will account for at least ⅛ of the area of the bottom of the lower lung lobe. Preferably, the area of the prosthesis projected to the bottom of the lower lung lobe will account for at least ¼ of the area of the bottom of the lower lung lobe. Preferably, the area of the prosthesis projected to the bottom of the lower lung lobe will account for at least half of the area of the bottom of the lower lung lobe. Preferably, the area of the prosthesis projected to the bottom of the lower lung lobe will occupy at least ¾ of the area of the bottom of the lower lung lobe. Preferably, the area of the prosthesis projected to the bottom of the lower lung lobe will account for the whole area of the bottom of the lower lung lobe.

The prosthesis in the present invention comprises a body having an upper side, a lower side and a lateral side extending between the upper side and the lower side. The prosthesis upper side is preferably matched with the basal of the lobes. The prosthesis lower side is preferably matched with the diaphragm. The prosthesis outer lateral side is preferably matched with the wall of pleural cavity between the bottom of the lobes and the diaphragm far away from the heart. The prosthesis inner lateral side is preferably matched with the outer wall of the lower lung lobe. The prosthesis may be in a shape of plate, ellipse, irregular U, arc, conical, scapula, or irregular, and so on, so as to occupy the space under the lung lobes. The prosthesis has a smooth curved profile without edges and corners so as to reduce the discomfort and avoid injury to the pleura.

Alternatively, the prosthesis in the present invention comprises a body having an upper side, a lower side, a lateral side extending between the upper side and the lower side, and a medial border approaching the heart, wherein the lateral side is opposite to the medial border. The prosthesis upper side is preferably matched with the bottom of the lobes. The prosthesis down side is preferably matched with the diaphragm. The prosthesis outer lateral side is preferably matched with the wall of pleural cavity between the bottom of the lobes and the diaphragm far away from the heart. The prosthesis is in a shape of plate, ellipse, irregular U, arc, conical, scapula, or irregular, and so on, so as to occupy the space under the lung lobes. Preferably, the prosthesis upper side tapers toward the medial border. The prosthesis lower side tapers toward the medial border. The prosthesis has a smooth curved profile without edges and corners so as to reduce the discomfort and avoid injury to the pleura.

Preferably, the lateral side is at a height of 0.5 cm-8 cm. Preferably, the lateral side is at a height of 0.5 cm, 0.6 cm, 0.7 cm, 0.8 cm, 0.8 cm, 0.9 cm, 1 cm, 2 cm, 3 cm, 4 cm, 5 cm, 6 cm, 7 cm, or 8 cm.

Preferably, the thickness of the wall of the prosthesis is between 0.1-4 cm. Preferably, the thickness is 0.1 cm, 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 3 cm, or 4 cm.

Preferably, the prosthesis in the present invention is in a shape of arc, wherein the arc is matched with the lower edge of the lower lung lobe. Preferably, the arch is matched with at least ⅛ of the lower edge of the lower lung lobe far away from the heart. Preferably, the arch is matched with at least ¼ of the lower edge of the lower lung lobe far from the heart. Preferably, the arch is matched with at least ½ of the lower edge of the lower lung lobe far away from the heart. Preferably, the arch is matched with the overall length of the lower edge of the lower lung lobe.

Preferably, the prosthesis is at a height of 1 cm-4 cm. Preferably, the lateral side is at a height of 1 cm, 2 cm, 3 cm, or 4 cm.

Preferably, the prosthesis is designed to be placed in the pleural cavity, in particular, the prosthesis is placed at the lower side of the pleural cavity, so as to reduce the mechanical tension on the alveolar epithelium at the end of normal inspiratory. The prosthesis may be fixed in the pleural cavity, in particular, the prosthesis is placed at the lower side of the pleural cavity. For example, the prosthesis may be sutured to the wall of pleural cavity, in particular, the lower part of wall of pleural cavity. Preferably, the prosthesis is sutured to the wall of pleural cavity through the pinholes on the lateral side.

The prosthesis may be made of soft spongy latex, foam latex, 380 micron hollow fiber, gelatin foam, material, plastic sponge (Ivalon), polythene bag filled with fiberglass, rubber, silicone rubber, silicone gel, carbon materials involving carbon nanotube, grapheme, ultra-light porous carbon, hollow porous carbon, carbon fiber, carbon titanium alloy, and et., al.

The prosthesis may be solid, or the prosthesis may be a pocket or a sack, filled with fluid or jelly.

In the third place, the invention provides a method for treating pulmonary fibrosis, in particular, idiopathic pulmonary fibrosis (IPF), which involves a step of reducing the mechanical tension on the alveolar epithelium at the end of normal inspiratory. Preferably, the invention provides a method for treating pulmonary fibrosis, in particular, idiopathic pulmonary fibrosis (IPF), which involves placing prosthesis in the pleural cavity, in particular, the lower part of the pleural cavity, so as to reduce the level of mechanical tension on the alveolar epithelium at the end of normal inspiratory. The prosthesis may be fixed in the pleural cavity, in particular, the prosthesis is placed at the lower part of the pleural cavity. For example, the prosthesis may be sutured to the wall of pleural cavity, in particular, the lower part of the chest wall.

The prosthesis in the present invention may be designed to be placed under the pulmonary lobe, as long as at the end of normal inspiratory, the level of mechanical tension on the alveolar epithelium is reduced.

Preferably, the prosthesis is designed to be anchored under the lobes and above the diaphragm, and preferably, is designed to be matched with the basal of the lobes, as long as at the end of normal inspiratory, the level of mechanical tension on the alveolar epithelium is reduced.

Therefore, the prosthesis is surrounded by pleural fluid. Preferably, the prosthesis will occupy at least ⅛ of the space surrounded by the bottom of the lobes, diaphragm and the wall of pleural cavity at the end of normal inspiratory. Preferably, the prosthesis will occupy at least ¼ of the space surrounded by the bottom of the lobes, diaphragm and the wall of pleural cavity at the end of normal inspiratory. Preferably, the prosthesis will occupy at least half of the space surrounded by the bottom of the lobes, diaphragm and the wall of pleural cavity at the end of normal inspiratory. Preferably, the prosthesis will occupy at least ¾ of the space surrounded by the bottom of the lobes, diaphragm and the wall of pleural cavity at the end of normal inspiratory. Preferably, the prosthesis will occupy the whole space surrounded by the bottom of the lobes, diaphragm and the wall of pleural cavity at the end of normal inspiratory.

Therefore, the prosthesis is surrounded by pleural fluid. Preferably, the area of the prosthesis projected to the bottom of the lower lung lobe will account for at least ⅛ of the area of the bottom of the lower lung lobe. Preferably, the area of the prosthesis projected to the bottom of the lower lung lobe will account for at least ¼ of the area of the bottom of the lower lung lobe. Preferably, the area of the prosthesis projected to the bottom of the lower lung lobe will account for at least half of the area of the bottom of the lower lung lobe. Preferably, the area of the prosthesis projected to the bottom of the lower lung lobe will occupy at least ¾ of the area of the bottom of the lower lung lobe. Preferably, the area of the prosthesis projected to the bottom of the lower lung lobe will account for the whole area of the bottom of the lower lung lobe.

The prosthesis in the present invention comprises a body having an upper side, a lower side and a lateral side extending between the upper side and the lower side. The prosthesis upper side is preferably matched with the bottom of the lobes. The prosthesis down side is preferably matched with the diaphragm. The prosthesis outer lateral side is preferably matched with the wall of pleural cavity between the bottom of the lobes and the diaphragm far away from the heart. The prosthesis inner lateral side is preferably matched with the out wall of the lower lung lobe. The prosthesis may be in a shape of plate, ellipse, irregular U, arc, conical, scapula, or irregular, and so on, so as to occupy the space under the lung lobes. The prosthesis has a smooth curved profile without edges and corners so as to reduce the discomfort and avoid injury to the pleura.

Alternatively, the prosthesis in the present invention comprises a body having an upper side, a lower side, a lateral side extending between the upper side and the lower side, and a medial border approaching the heart, wherein the lateral side is opposite to the medial border. The prosthesis upper side is preferably matched with the basal of the lobes. The prosthesis lower side is preferably matched with the diaphragm. The prosthesis outer lateral side is preferably matched with the wall of pleural cavity between the bottom of the lobes and the diaphragm far from the heart. The prosthesis is in a shape of plate, ellipse, irregular U, arc, conical, scapula, or irregular, and so on, so as to occupy the space under the lung lobes. Preferably, the prosthesis upper side tapers toward the medial border. The prosthesis lower side tapers toward the medial border. The prosthesis has a smooth curved profile without edges and corners so as to reduce the discomfort and avoid injury to the pleura.

Preferably, the lateral side is at a height of 0.5 cm-8 cm. Preferably, the lateral side is at a height of 0.5 cm, 0.6 cm, 0.7 cm, 0.8 cm, 0.8 cm, 0.9 cm, 1 cm, 2 cm, 3 cm, 4 cm, 5 cm, 6 cm, 7 cm, or 8 cm.

Preferably, the thickness of the wall of the prosthesis is between 0.1-4 cm. Preferably, the thickness is 0.1 cm, 0.2 cm, 0.3 cm, 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 3 cm, or 4 cm.

Preferably, the prosthesis in the present invention is in a shape of arc, wherein the arc is matched with the lower edge of the lower lung lobe. Preferably, the arch is matched with at least ⅛ of the lower edge of the lower lung lobe far away from the heart. Preferably, the arch is matched with at least ¼ of the lower edge of the lower lung lobe far away from the heart. Preferably, the arch is matched with at least ½ of the lower edge of the lower lung lobe far away from the heart. Preferably, the arch is matched with the overall length of the lower edge of the lower lung lobe.

Preferably, the prosthesis is at a height of 1 cm-4 cm. Preferably, the lateral side is at a height of 1 cm, 2 cm, 3 cm, or 4 cm.

Preferably, the prosthesis is designed to be placed in the pleural cavity, in particular, the prosthesis is placed at the lower side of the pleural cavity, so as to reduce the mechanical tension on the alveolar epithelium at the end of normal inspiratory. The prosthesis may be fixed in the pleural cavity, in particular, the prosthesis is placed at the lower side of the pleural cavity. For example, the prosthesis may be sutured to the pleural cavity wall, in particular, the lower part of the pleural cavity wall. Preferably, the prosthesis is sutured to the wall of pleural cavity through the pinholes on the lateral side.

The prosthesis may be made of soft spongy latex, foam latex, 380 micron hollow fiber, gelatin foam, material, plastic sponge (Ivalon), polythene bag filled with fiberglass, rubber, silicone rubber, silicone gel, carbon materials involving carbon nanotube, grapheme, ultra-light porous carbon, hollow porous carbon, carbon fiber, carbon titanium alloy, and et., al.

The prosthesis may be solid, or the prosthesis may be a pocket or a sack, filled with fluid or jelly.

The invention encompasses all combinations of the particular embodiments recited herein.

The invention encompasses all combination of the particular embodiments recited herein. Idiopathic pulmonary fibrosis (IPF) is a fatal progressive lung disease with few treatment options. Our invention demonstrates that impaired alveolar regeneration results in elevated mechanical tension that in turn drives the initiation and progression of lung fibrosis. We establish that prosthesis implantation in the pleural cavity, a simple therapeutic approach, greatly attenuates the progression of lung fibrosis. We anticipate that prosthesis implantation will lead to major breakthroughs to advance the future development of treatments for IPF. Therefore, the present invention is a pioneering invention, which achieves the treatment of IPF, a difficult disease in the world.

BRIEF DESCRIPTION OF THE DRAWINGS

FIG. 25 shows the fragments of Cdc42 DNA sequence before or after deleting the exon2 of the Cdc42 gene.

DESCRIPTION OF PARTICULAR EMBODIMENTS OF THE INVENTION

Figures 1A, 1B, 1C, 1D, 1E, 1F:
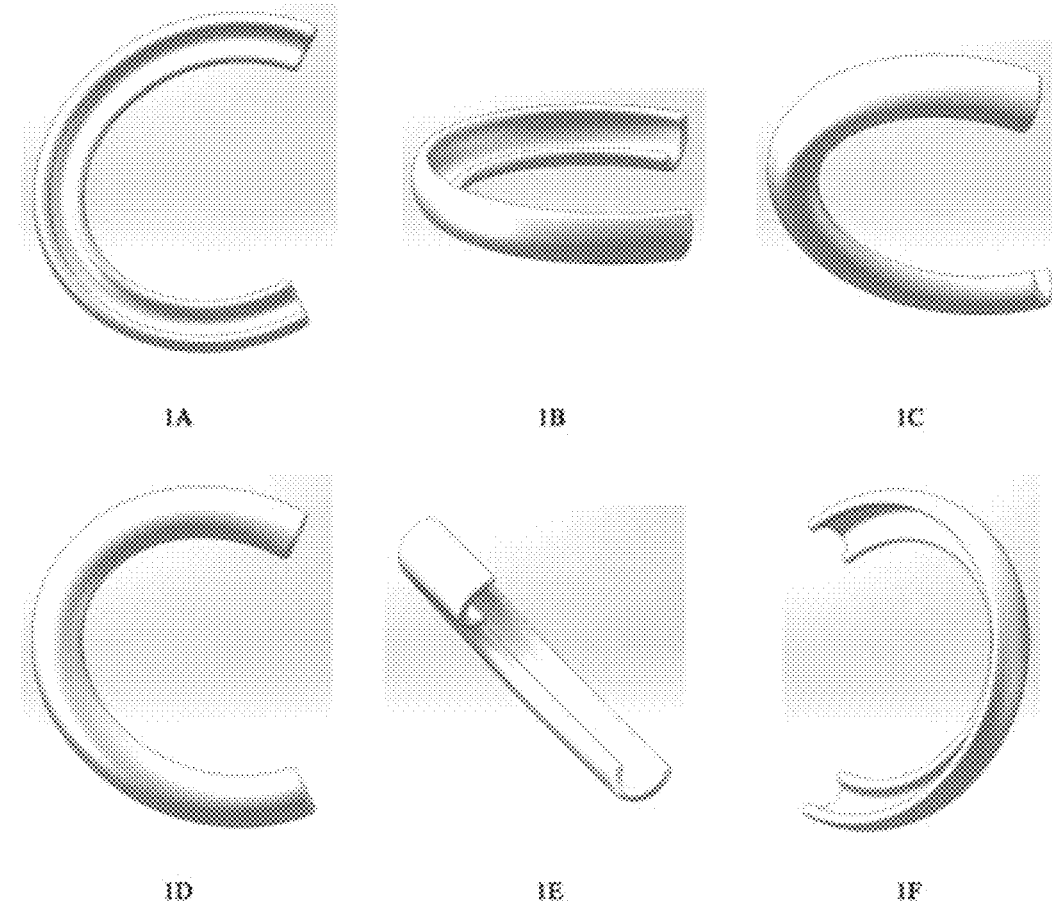
FIGS. 1A-1F show six perspectives of a prosthesis manufactured in accordance with the present invention.
Figures 2A, 2B, 2C, 2D:
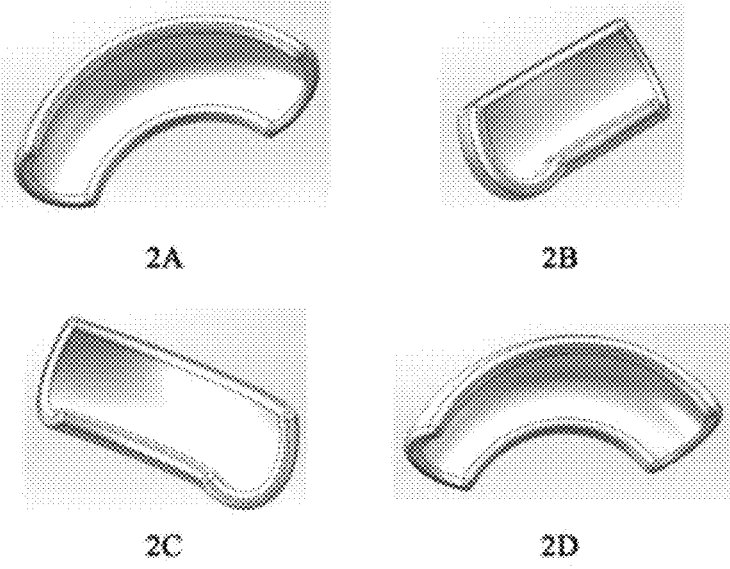
FIGS. 2A-2D show four perspectives of a prosthesis manufactured in accordance with the present invention.
Figures 3A, 3B, 3C, 3D:
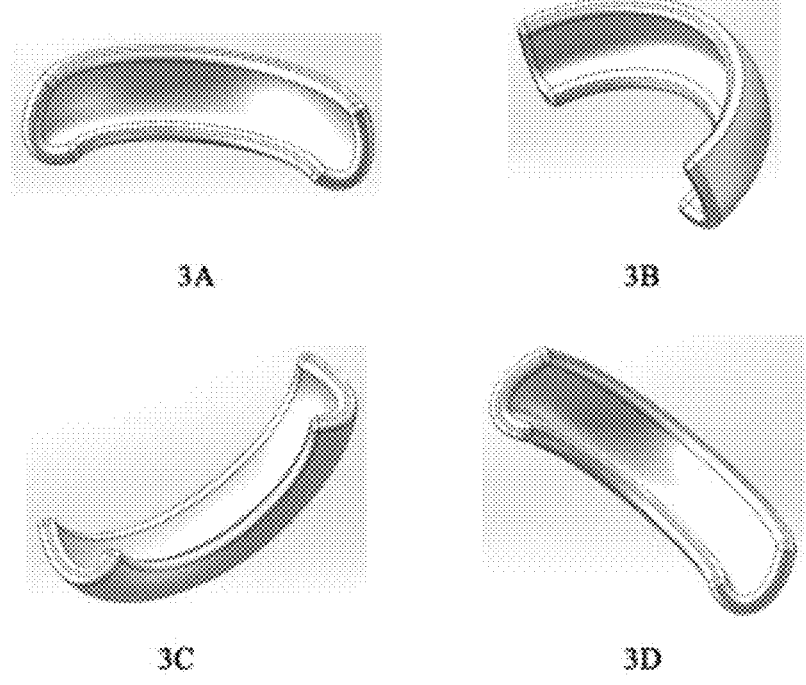
FIGS. 3A-3D show four perspectives of a prosthesis manufactured in accordance with the present invention.
Figures 4A, 4B, 4C, 4D, 4E, 4F:
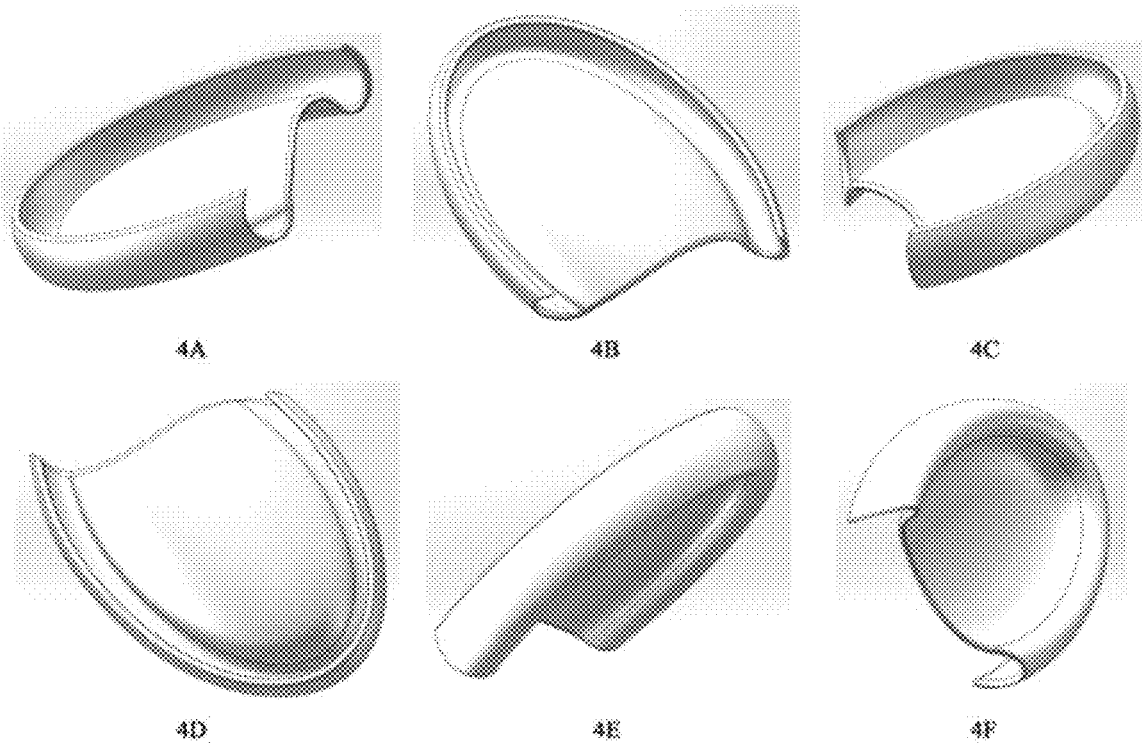
FIGS. 4A-4F show six perspectives of a prosthesis manufactured in accordance with the present invention.
Figures 5A, 5B, 5C, 5D, 5E:
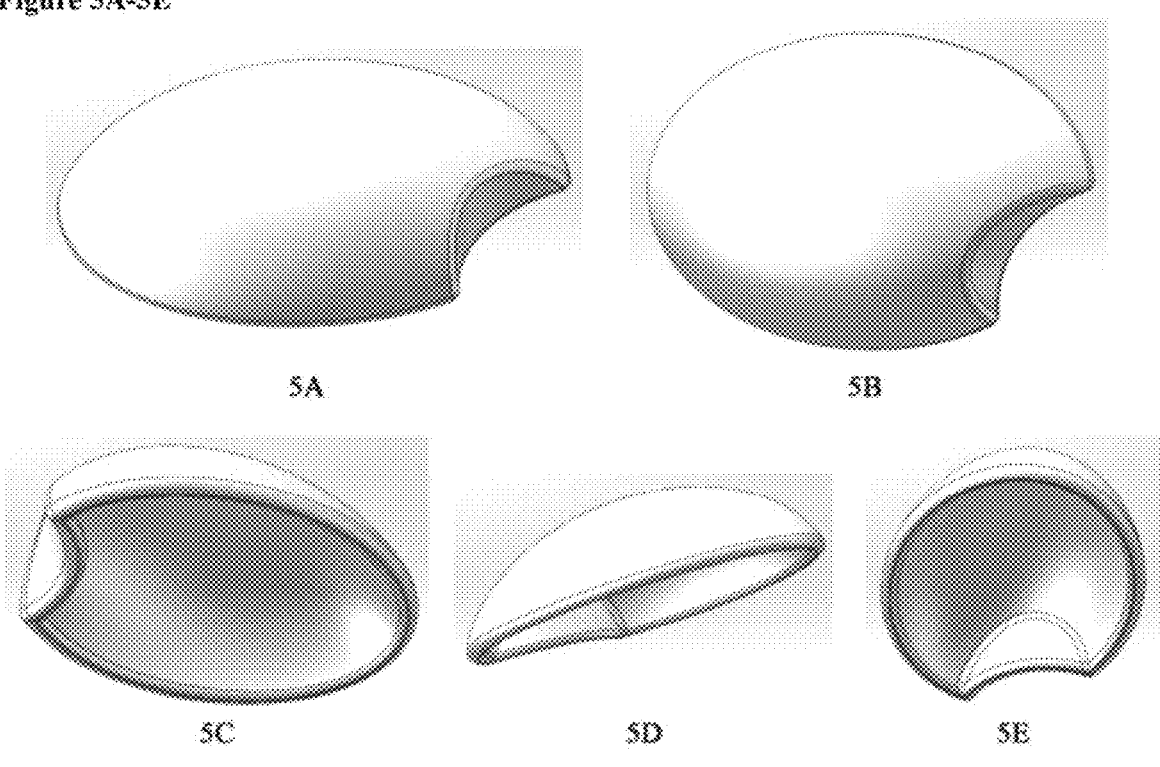
FIGS. 5A-5E show five perspectives of a prosthesis manufactured in accordance with the present invention.
Figures 6A, 6B, 6C, 6D, 6E, 6F:
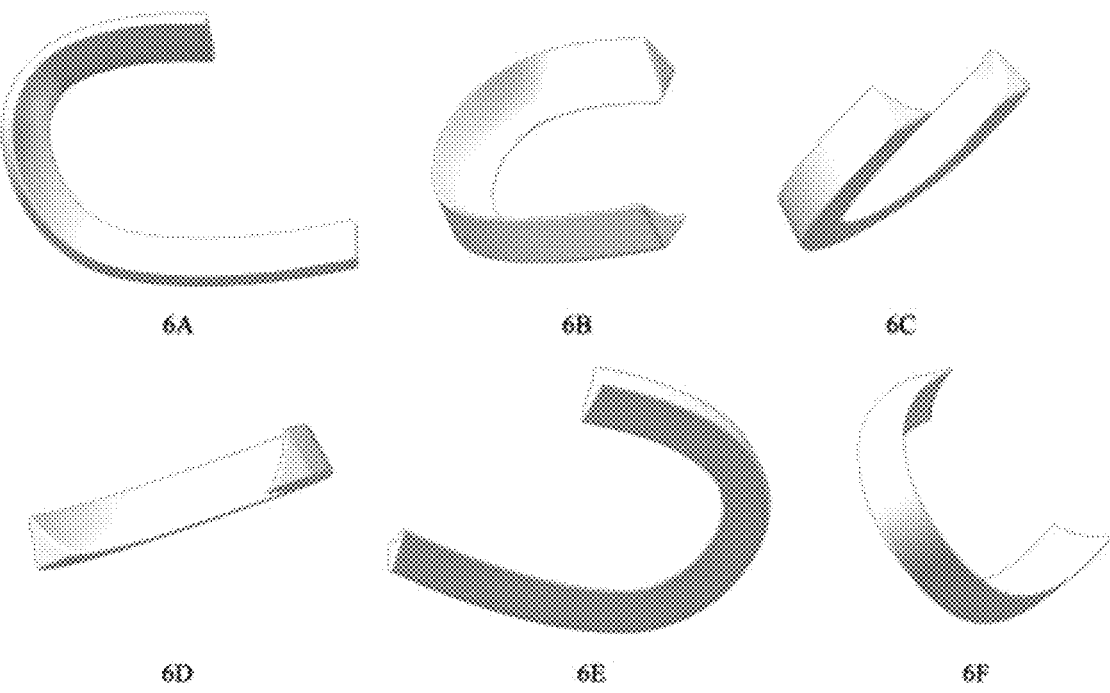
FIGS. 6A-6F show six perspectives of a prosthesis manufactured in accordance with the present invention.

The descriptions of particular embodiments and examples are provided by way of illustration and not by way of limitation. Those skilled in the art will readily recognize a variety of noncritical parameters that could be changed or modified to yield essentially similar results.

The pleural cavity is the thin fluid-filled space between the two pulmonary pleurae (known as visceral and parietal) of each lung. A pleura is a serous membrane which folds back onto itself to form a two-layered membranous pleural sac. The outer pleura (parietal pleura) is attached to the chest wall, but is separated from it by the endothoracic fascia. The inner pleura (visceral pleura) covers the lung and adjacent structures, including blood vessels, bronchi and nerves. The pleural cavity can be viewed as a potential space because the two pleurae adhere to each other (through the thin film of serous liquid) under all normal conditions. The pleural cavity is surrounded by the rib cage, and it surrounds the lungs. A small amount of fluid is located in the potential space between the two layers of the pleura.

Pleural fluid is serous fluid produced by the serous membrane covering normal pleurae. Most fluid is produced by the parietal circulation (intercostal arteries) via bulk flow and reabsorbed by the lymphatic system. Thus, pleural fluid is produced and reabsorbed continuously.

The lungs are located in the chest on both sides of the heart in the rib cage. They are conical in shape with a narrow rounded apex at the top, and a broad concave base that rests on the convex surface of the diaphragm. The lungs are surrounded by the pulmonary pleurae. The pleurae are two serous membranes; the outer parietal pleura lines on the inner wall of the rib cage and the inner visceral pleura directly lines on the surface of the lungs. Between the pleurae is a potential space called the pleural cavity, which contains a thin layer of lubricating pleural fluid. Each lung is divided into lobes by the infoldings of the pleura as fissures. The fissures are double folds of pleura that separates the lungs and helps the lung to expand. The right lung has three lobes, namely, the superior (upper), middle and inferior (lower) lobes, and there are only two lobes in the left lung: the superior (upper) and inferior (lower) lung lobes.

The term "mechanical tension" in the present invention means "physical tension", "stretch", "distension", "stress", or "strain", for example, "strain" involves "compressive strain", "tensile strain", and an angular distortion is a "shear strain".

The idiopathic pulmonary fibrosis (IPF) is a type of chronic lung disease characterized by progressive and irreversible decline in lung function. Symptoms typically include gradual shortness of breath and a dry cough. Other changes may include feeling tired and nail clubbing. Complications may include pulmonary hypertension, heart failure, pneumonia, or pulmonary embolism.

Prosthesis is an artificial device that replaces a body part and is intended to restore the normal functions of the body part. Prostheses can be made by hand or with CAD (Computer-Aided Design), a software interface that helps creators to visualize the creation in a 3D form. The prosthetics are made in lightweight to facilitate the subject, and some of the materials include: plastics (polyethylene, polypropylene, acrylics, polyurethane), lightweight metals (titanium, aluminum), composite (carbon fibre), and silicone rubber.

Surgical suture is used to hold body tissues together after an injury or surgery. Surgical suture is made from numerous materials. The original suture is made from biological materials, such as catgut suture and silk, and synthetic materials, such as absorbable polyglycolic acid, polylactic acid, monocryl and polydioxanone as well as the non-absorbable nylon, polyester, PVDF and polypropylene. The polymer materials are based on one or more of five cyclic monomers: glycolide, 1-lactide, p-dioxanone, trimethylene carbonate and c-caprolactone.

Silicone rubber is an elastomer composed of silicone, a polymer, containing silicon together with carbon, hydrogen, and oxygen. Silicone rubber offers properties such as good resistance to extreme temperatures, elongation, creep, cyclic flexing, tear strength, compression set, dielectric strength (at high voltage), thermal conductivity, fire resistance and in some cases tensile strength can be—at extreme temperatures—far superior to organic rubbers in general.

The persons skilled in the art will anticipate that any drugs or prosthesis that reducing the mechanical tension of alveolar epithelium will be involved in the scope of the invention, since the inventors of the present invention firstly establish a direct linkage between the mechanical tension and the IPF, that is to say, reducing the mechanical tension of alveolar epithelium will be effective.

EXAMPLES

Methods

Mice and Survival Curve Record

Rosa26-CAG-mTmG (Rosa26-mTmG)[20] and Cdc42$^{flox/flox}$ mice[21] have been described previously. All experiments were performed in accordance with the recommendations in the Guide for Care and Use of Laboratory Animals of the National Institute of Biological Sciences. To monitor the survival of mice, both the Control and the Cdc42 AT2 null mice were weighed every week after the PNX treatment. Once the mice reached the pre-defined criteria for endpoints, the mice were sacrificed. We define the endpoints according to the pre-defined criteria[22,23].

Generating Spc-CreER Knock-in Allele

The CreERT2, p2a, and rtTA element were enzyme-linked and inserted into the mouse endogenous Sftpc gene. The insertion site is the stop codon of the endogenous Sftpc gene, then a new stop codon was created at the 3' end of rtTA. The CRISPR/Cas9 technology was used to insert the CreERT2-p2a-rtTA fragment into the genome.

Pneumonectomy (PNX) and Prosthesis Implantation

The male mice of 8 weeks old were injected with tamoxifen (dosage: 75 mg/kg) every other day for 4 times. The mice were anesthetized and connected to a ventilator (Kent Scientific, Topo) from 14th day after the final dose of tamoxifen injection. The chest wall was incised at the fourth intercostal ribs and the left lung lobe was removed. For prosthesis implantation, a soft silicone prosthesis with a similar size and shape of the left lung lobe was inserted into the empty left lung cavity.

Pulmonary Function Test

Lung function parameters were measured using the invasive pulmonary function testing system (DSI Buxco® PFT Controller). Mice were first anesthetized before inserting an endotracheal cannula into their trachea. The dynamic compliance results were obtained from the Resistance & Compliance Test.

Hematoxylin and Eosin (H&E) Staining and Immunostaining

Lungs were inflated with 4% paraformaldehyde (PFA) and were continually fixed in 4% PFA at 4° C. for 24 hours. Then the lungs were cryoprotected in 30% sucrose and embedded in OCT (Tissue Tek).

The H&E staining experiment followed the standard H&E protocol. Briefly, slides were washed by water to remove the OCT. The nuclei were stained by hemotoxylin (Abcam, ab150678) for 2 minutes and the cytoplasm was stained by eosin (Sigma, HT110280) for 3 minutes. Slices were sealed with neutral resin after the dehydration and clearing steps.

The immunofluorescence staining experiments followed the protocol previously described[24]. In brief, after removing the OCT, the lung slices were blocked with 3% BSA/0.1% TritonX-100/PBS for 1 hour, then slides were incubated with primary antibodies at 4° C. for overnight. After washing the slides with 0.1% TritonX-100/PBS for 3 times, the slices were incubated with secondary antibodies for 2 hours at room temperature.

The primary antibodies used in the paper are listed below:

| Name | Company and catalog number | Dilution |
| --- | --- | --- |
| Chicken anti-GFP | Abcam, ab13970-100 | 1:500 |
| Rabbit anti-Collagen I | Abcam, ab34710 | 1:300 |
| Mouse anti α-SMA | Sigma, C6198 | 1:300 |
| Hamster anti-Pdpn | Developmental Studies Hybridoma Bank, clone8.1.1 | 1:100 |
| Rat anti-Ki67 | Bioscience, 514-5698-82 | 1:300 |

The secondary antibodies used in the paper are listed below:

| Name | Company and catalog number | Dilution |
| --- | --- | --- |
| Alexa Fluor 488 Donkey anti-Chicken | 703-545-155, Jackson Immuno Research | 1:500 |
| Alexa Fluor 488 Donkey anti-mouse | 715-545-150, Jackson Immuno Research | 1:500 |
| Alexa Fluor 568 Donkey anti-rabbit | A11057, Invitrogen | 1:500 |
| Alexa Fluor 647 Goat anti-hamster | A-21451, Invitrogen | 1:500 |
| Biotin Donkey Anti-Rabbit | 711-065-152, Jackson Immuno Research | |

Statistical Analysis

All data are presented as mean±s.e.m. (as indicated in figure legends). The data presented in the figures were collected from multiple independent experiments that were performed on different days using different mice. Unless otherwise mentioned, most of the data presented in figure panels are based on at least three independent experiments. The inferential statistical significance of differences between sample means was evaluated using two-tailed unpaired Student's t-tests.

Isolating Mouse AT2 Cells

After 4 doses of tamoxifen injection, the lungs of Spc-CreER, Rosa26-mTmG mice were dissociated as previously described[19,44]. Briefly, anesthetized mice were inflated with neutral protease (Worthington-Biochem, LS02111) and DNase I (Roche, 10104159001). AT2 cells were directly sorted based on the GFP fluorescence using the single-cell-select-mode in BD FACS Aria II and III appliances.

Quantitative RT-PCR (qPCR)

Total RNA was isolated from either whole lung or primary AT2 cells using Zymo Research RNA Mini Prep Kits (R2050). Reverse transcription reactions were performed with a two-step cDNA synthesis Kit (Takara, Cat. #6210A/B) according to the manufacturer's recommendations. qPCR was done with a CFX96 Touch™ Real-Time PCR Detection System. The mRNA levels of target genes were normalized to the Gapdh mRNA level.

Primers used for qPCR are listed below.

| | Forward | Reverse |
| --- | --- | --- |
| Gapdh | AAGGTCGGTGTGAACGGATTTGG (SEQ ID NO: 1) | CGTTGAATTTGCCGTGAGTGGAG (SEQ ID NO: 2) |
| Sftpc | TTGTCGTGGTGATTGTAGGG (SEQ ID NO: 3) | TGGAAAAGGTAGCGATGGTG (SEQ ID NO: 4) |
| Scd1 | GCAAGCTCTACACCTGCCTCTT (SEQ ID NO: 5) | CGTGCCTTGTAAGTTCTGTGGC (SEQ ID NO: 6) |
| Lyz2 | TGCCAGAACTCTGAAAAGGAATGG (SEQ ID NO: 7) | CAGTGCTTTGGTCTCCACGGTT (SEQ ID NO: 8) |
| Cbr2 | CATGGGCAAGAAAGTCTCTGCAG (SEQ ID NO: 9) | ACTGGTAGAGGCACTTCTGTCG (SEQ ID NO: 10) |
| Sftpa1 | ACCTGGATGAGGAGCTTCAGAC (SEQ ID NO: 11) | CTGACTGCCCATTGGTGGAAAAG (SEQ ID NO: 12) |
| Actb | CATTGCTGACAGGATGCAGAAGG (SEQ ID NO: 13) | TGCTGGAAGGTGGACAGTGAGG (SEQ ID NO: 14) |
| Actn1 | TCGCCAAGTGTCAACGCTCGTT (SEQ ID NO: 15) | GGTCGATGGTTTCCAGCAGCTT (SEQ ID NO: 16) |
| Pfn1 | CATCGTAGGCTACAAGGACTCG (SEQ ID NO: 17) | CCAAGTGTCAGCCCATTGACGA (SEQ ID NO: 18) |
| Ezr | ATCGAGGTGCAGCAGATGAAGG (SEQ ID NO: 19) | CGGAGCATCTGCTCCTTTTCTC (SEQ ID NO: 120) |
| Gsn | GGCTTTGAGTCGTCCACCTTCT (SEQ ID NO: 21) | GTCCTTTGACCTGGAAGAGCCT (SEQ ID NO: 22) |

3D Alveolar Reconstruction

For vibratome sections, lungs were gently inflated to full capacity with 2% low-melting agarose. Then lungs were fixed in 4% PFA for overnight at 4° C. Thick vibratome sections were sliced at a thicknesses of 200 μm using the vibrating microtome (Leica VT100S). Immunostaining experiments were performed as the standard wholemount staining protocol. Z stack images were taken by Leica LSI macro confocal microscope and/or A1-R inverted confocal microscope.

CDC42-GTP Assay

The GTP-CDC42 level is determined using the CDC42 activation assay biochem kit (cytoskeleton, #BK127) according to the provided manufacturer's recommendations. Briefly, the whole lung lobes were grinded in liquid nitrogen, then lysed using the cell lysis buffer (applied in the kit). Then the cell lysates were added into the microplate wells applied. After the reaction, the absorbance at 490 nm was measured.

Example 1

As shown in FIGS. 1A-1F, the prosthesis is in a shape of arc and occupies about ¾ of the edge of the lower part of the lung lobe. The lateral side has a height of about 1.5 cm. The prosthesis has a thickness of about 2 mm. The bottom of the prosthesis has a width of 1 cm. The prosthesis may be sewed onto the wall of pleural cavity. The sides of the prosthesis are round and smooth as far as possible.

The opening is toward the heart. At the end of normal inspiratory, the prosthesis presses the lower part of the lung lobe and the mechanical tension of alveolar epithelium is reduced.

Example 2

As shown in FIGS. 2A-2D, the prosthesis is in a shape of arc and occupies about ⅛ of the edge of the lower part of the lung lobe. The lateral side has a height of about 3 cm. The prosthesis has a thickness of about 7 mm. The bottom of the prosthesis has a width of 2 cm. The prosthesis may be sewed onto the side wall of pleural cavity far from the heart. The sides of the prosthesis are round and smooth as far as possible.

At the end of normal inspiratory, the prosthesis presses the lower part of the lung lobe and the mechanical tension of alveolar epithelium is reduced.

Example 3

As shown in FIGS. 3A-3D, the prosthesis is in a shape of arc and occupies about ¼ of the edge of the lower part of the lung lobe. The lateral side has a height of about 3 cm. The prosthesis has a thickness of about 6 mm. The bottom of the prosthesis has a width of 1.3 cm. The prosthesis may be sewed onto the side wall of pleural cavity far from the heart. The sides of the prosthesis are round and smooth as far as possible.

At the end of normal inspiratory, the prosthesis presses the lower part of the lung lobe and the mechanical tension of alveolar epithelium is reduced.

Example 4

As shown in FIGS. 4A-4F, the prosthesis is in a shape of plate and matches the whole area of the basal of the lower lung lobe. The lateral side has a height of about 2.5 cm. The prosthesis has a thickness of about 2 mm. The prosthesis may be sewed onto the side wall of pleural cavity. The sides of the prosthesis are round and smooth as far as possible.

At the end of normal inspiratory, the prosthesis presses the lower part of the lung lobe and the level of mechanical tension of alveolar epithelium is reduced.

Example 5

As shown in FIGS. 5A-5E, the prosthesis is in a shape of shell-like and matches the whole area of the bottom of the lower lung lobe. The prosthesis has depression in the middle and tapers to the side wall of pleural cavity. The prosthesis also has a depression on the side of heart to hold the heart. The prosthesis has a thickness of about 4 mm. The sides of the prosthesis are round and smooth as far as possible.

At the end of normal inspiratory, the prosthesis presses the lower part of the lung lobe and the mechanical tension of alveolar epithelium is reduced.

Example 6

As shown in FIGS. 6A-6F, the prosthesis is in a shape of U-like and matches more than ¾ of the edge of the lower lung lobe. The section of the prosthesis is close to triangle. The side touching the edge of the lower lung lobe is a concave arc. The outer side of the prosthesis has height of 1.0 cm. The sides of the prosthesis are round and smooth as far as possible.

The prosthesis may be sewed onto the side wall of pleural cavity. At the end of normal inspiratory, the prosthesis presses the lower part of the lung lobe and the mechanical tension of alveolar epithelium is reduced.

Example 7

Figures 7A, 7B, 7C:
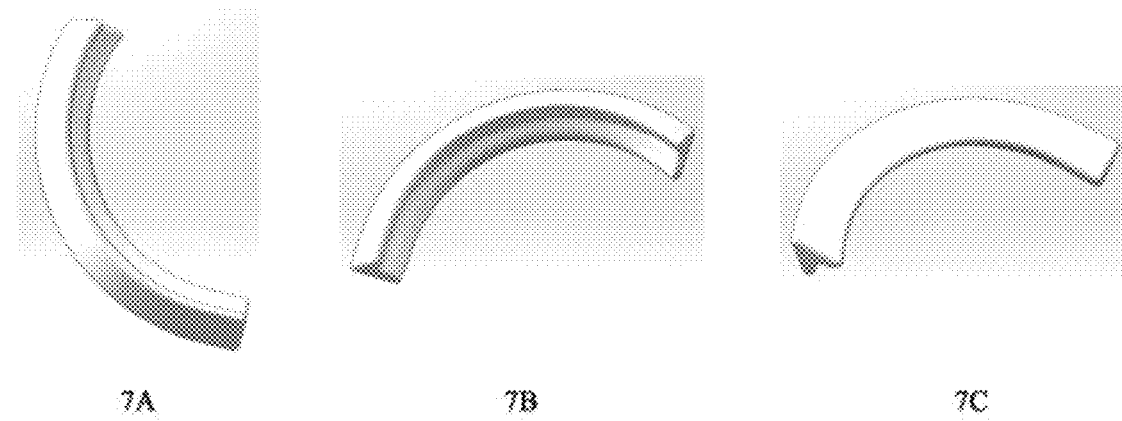
FIGS. 7A-7C show three perspectives of a prosthesis manufactured in accordance with the present invention.

As shown in FIGS. 7A-7C, the prosthesis is in a shape of arc and matches more than ¼ of the edge of the lower lung lobe. The section of the prosthesis is close to triangle. The side touching the edge of the lower lung lobe is a concave arc. The outer side of the prosthesis has a height of 1.6 cm. The sides of the prosthesis are round and smooth as far as possible.

The prosthesis may be sewed onto the side wall of pleural cavity far from the heart. At the end of normal inspiratory, the prosthesis presses the lower part of the lung lobe and the mechanical tension of alveolar epithelium is reduced.

Example 8

Figures 8A, 8B, 8C:
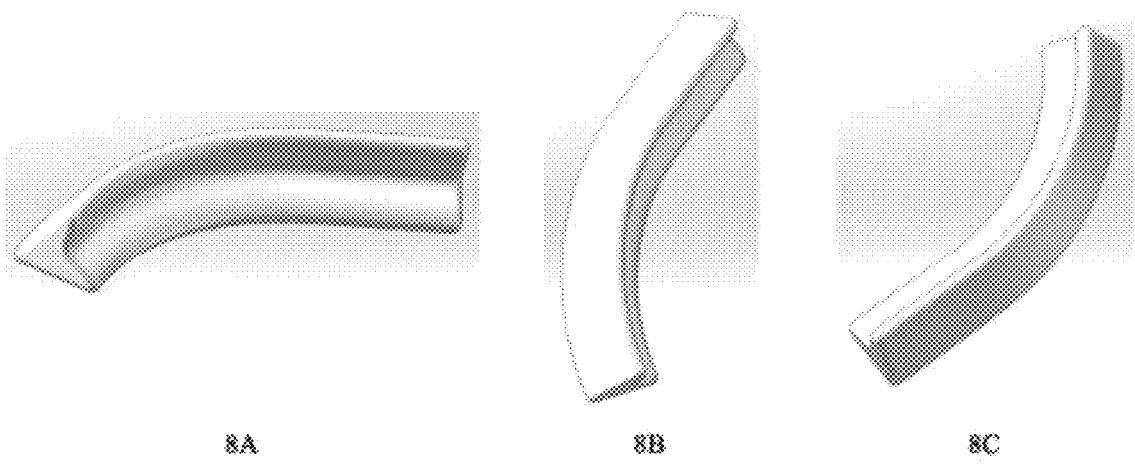
FIGS. 8A-8C show three perspectives of a prosthesis manufactured in accordance with the present invention.

As shown in FIGS. 8A-8C, the prosthesis is in a shape of arc and matches more than ¼ of the edge of the lower lung lobe. The prosthesis has a smaller radian than the prosthesis in Example 7. The section of the prosthesis is close to triangle. The side touching the edge of the lower lung lobe is a concave arc. The outer side of the prosthesis has a height of 2.2 cm. The sides of the prosthesis are round and smooth as far as possible.

The prosthesis may be sewed onto the side wall of pleural cavity far from the heart. At the end of normal inspiratory, the prosthesis presses the lower part of the lung lobe and the mechanical tension of alveolar epithelium is reduced.

Example 9

Figures 9A, 9B, 9C:
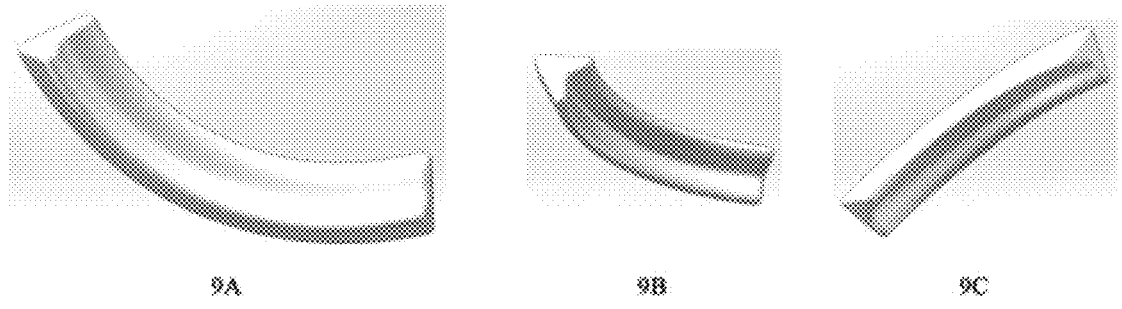
FIGS. 9A-9C show three perspectives of a prosthesis manufactured in accordance with the present invention.

As shown in FIGS. 9A-9C, the prosthesis is in a shape of arc and matches more than ⅛ of the edge of the lower lung lobe. The prosthesis has a smaller radian than the prosthesis in Example 7. The section of the prosthesis is close to triangle. The side touching the edge of the lower lung lobe is a concave arc. The outer side of the prosthesis has a height of 3.5 cm. The sides of the prosthesis are round and smooth as far as possible.

The prosthesis may be sewed onto the side wall of pleural cavity far from the heart. At the end of normal inspiratory, the prosthesis presses the lower part of the lung lobe and the mechanical tension of alveolar epithelium is reduced.

Example 10

Figures 10A, 10B, 10C:
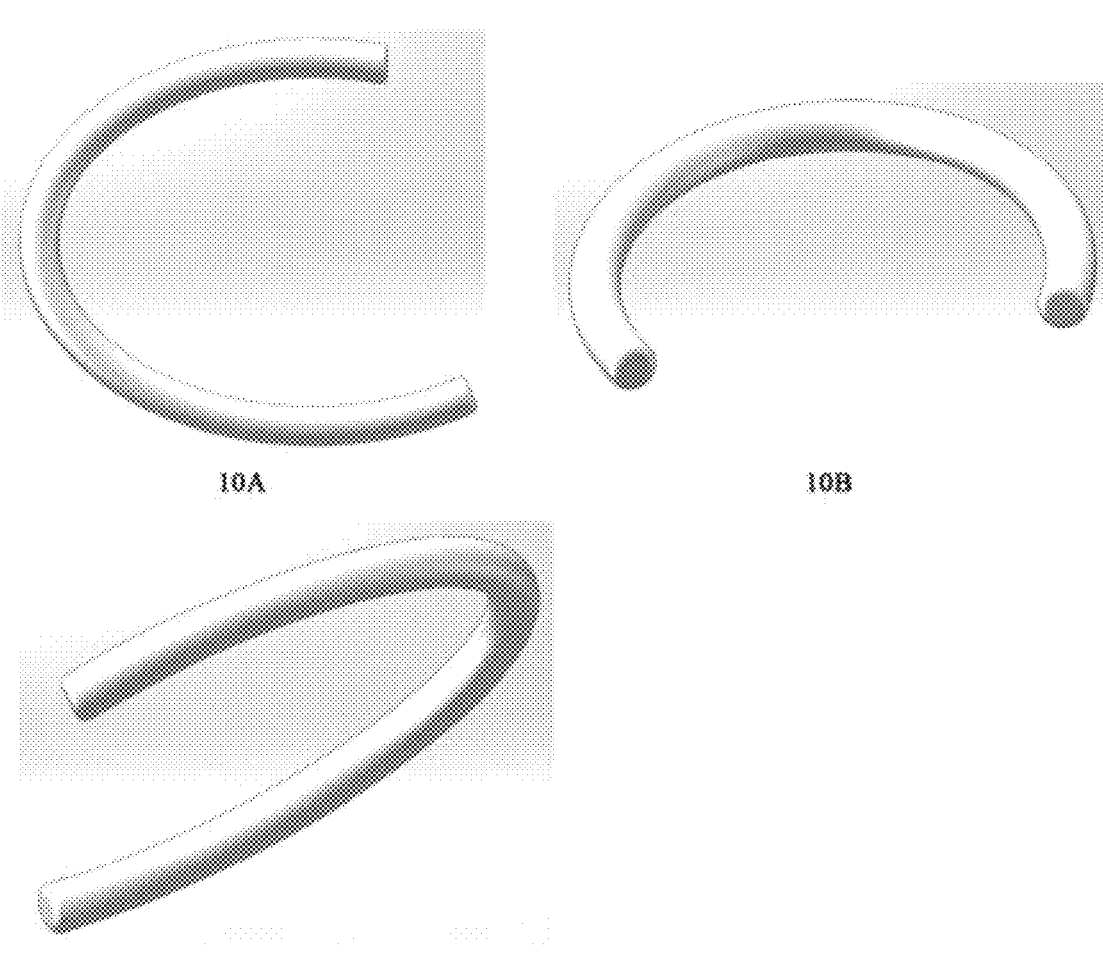
FIGS. 10A-10C show three perspectives of a prosthesis manufactured in accordance with the present invention.

As shown in FIGS. 10A-10C, the prosthesis is in a shape of circular arc and matches more than ¾ of the edge of the lower lung lobe. The section of the prosthesis is close to circular. The radius of the section is about 0.5 cm.

At the end of normal inspiratory, the prosthesis presses the lower part of the lung lobe and the mechanical tension of alveolar epithelium is reduced.

Example 11

Figures 11A, 11B, 11C:
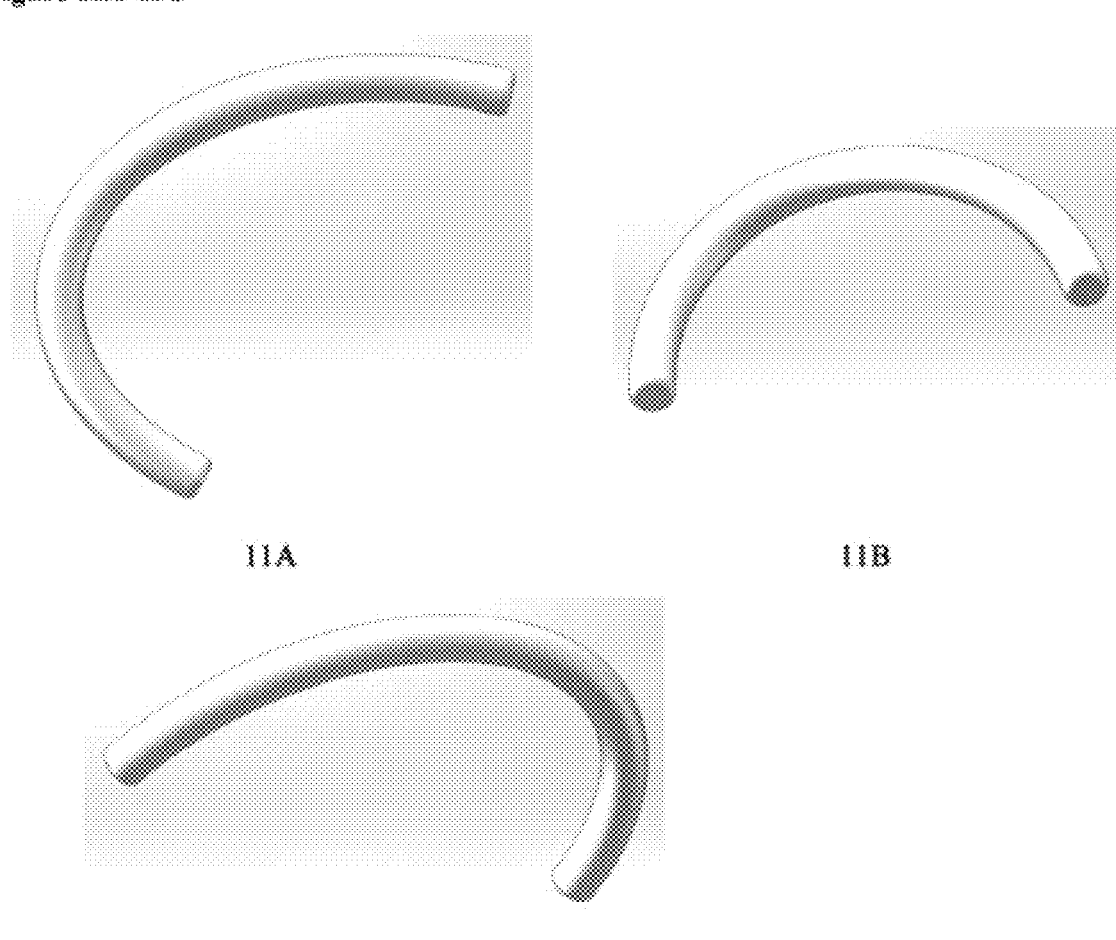
FIGS. 11A-11C show three perspectives of a prosthesis manufactured in accordance with the present invention.

As shown in FIGS. 11A-11C, the prosthesis is in a shape of arc and matches more than ¼ of the edge of the lower lung lobe. The section of the prosthesis is close to circular. The radius of the section is about 0.8 cm.

The prosthesis may be sewed onto the side wall of pleural cavity far from the heart. At the end of normal inspiratory, the prosthesis presses the lower part of the lung lobe and the mechanical tension of alveolar epithelium is reduced.

Example 12

Figures 12A, 12B, 12C:
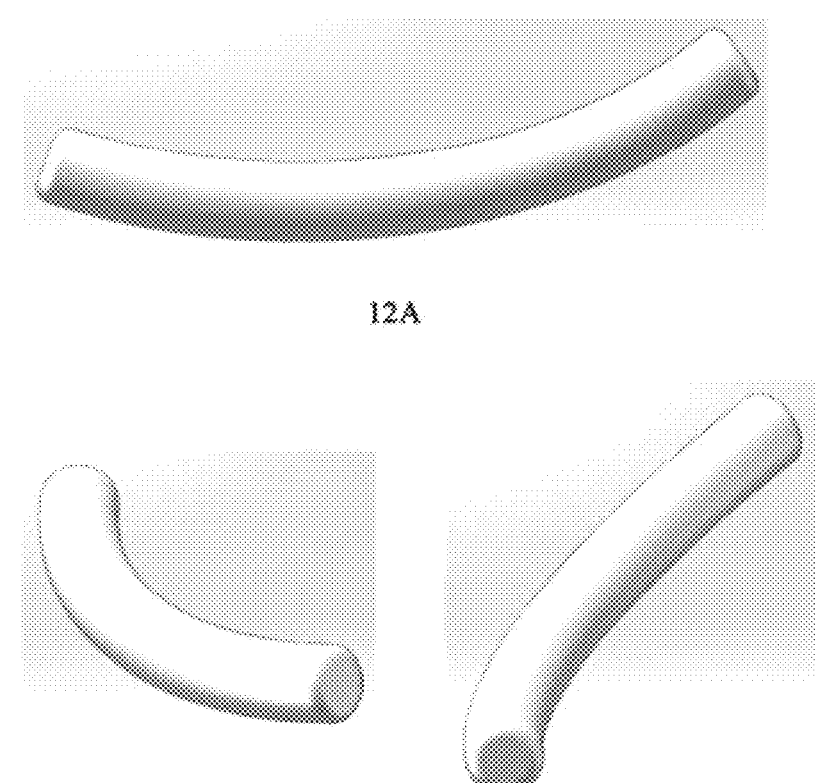
FIGS. 12A-12C show three perspectives of a prosthesis manufactured in accordance with the present invention.
Figures 13A, 13B, 13C, 13D:
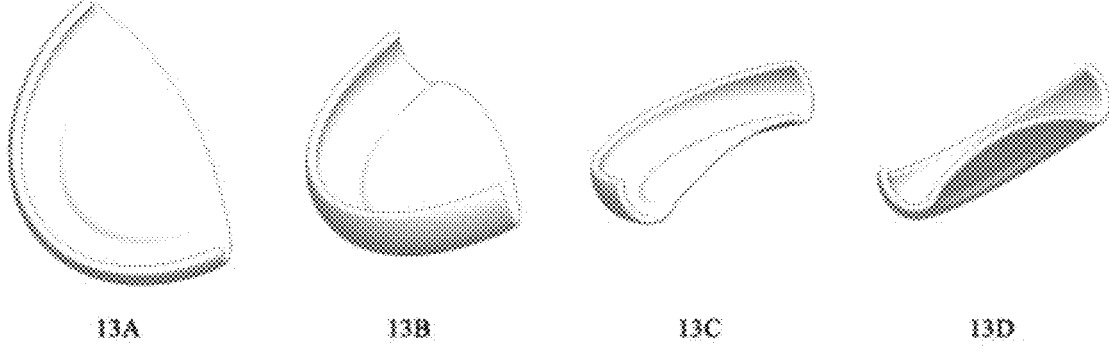
FIGS. 13A-13D show four perspectives of a prosthesis manufactured in accordance with the present invention.
Figures 14A, 14B, 14C, 14D:
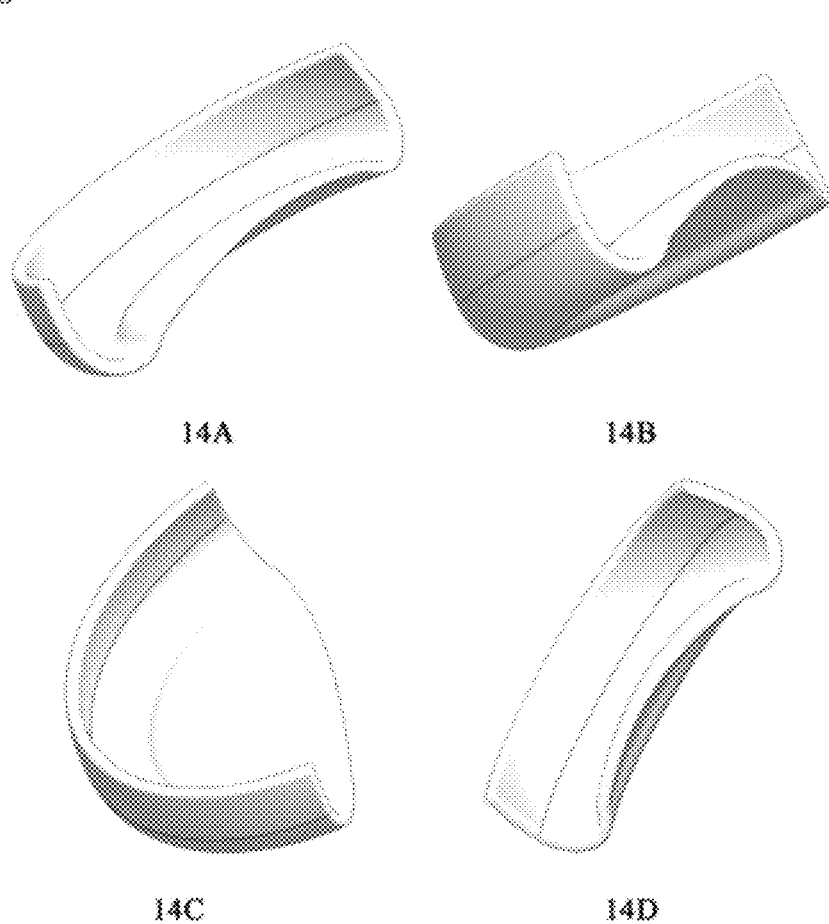
FIGS. 14A-14D show four perspectives of a prosthesis manufactured in accordance with the present invention.
Figures 15A, 15B, 15C, 15D:
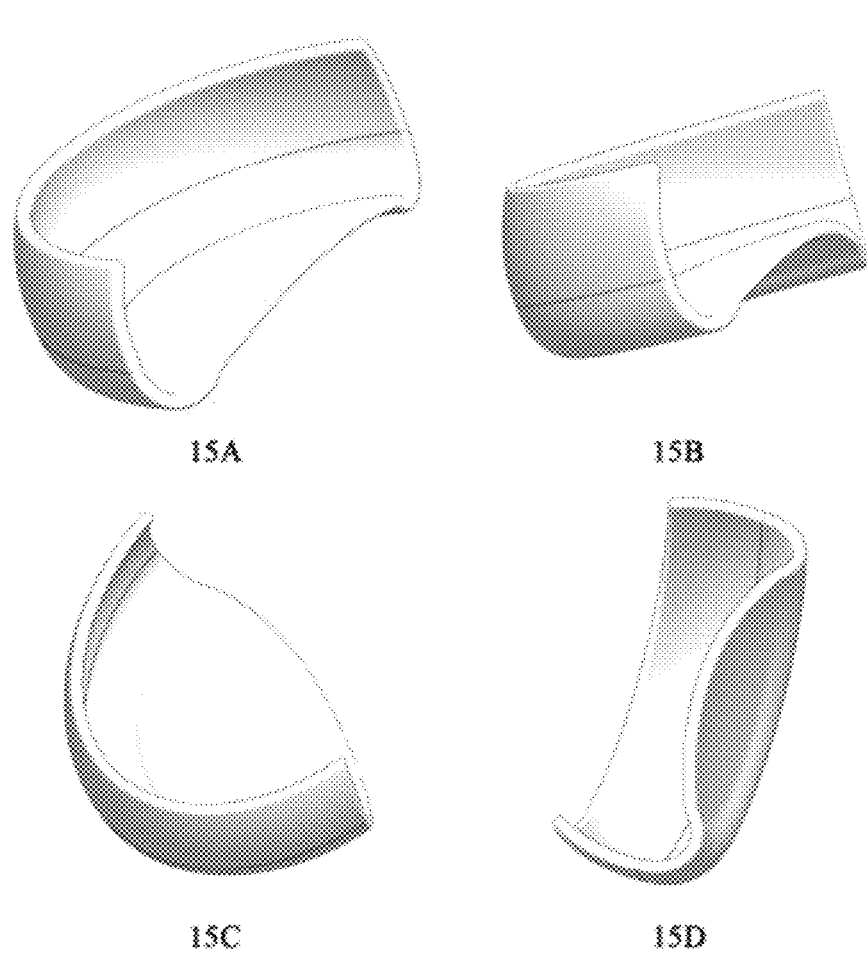
FIGS. 15A-15D show four perspectives of a prosthesis manufactured in accordance with the present invention.
Figures 16A, 16B, 16C, 16D, 16E:
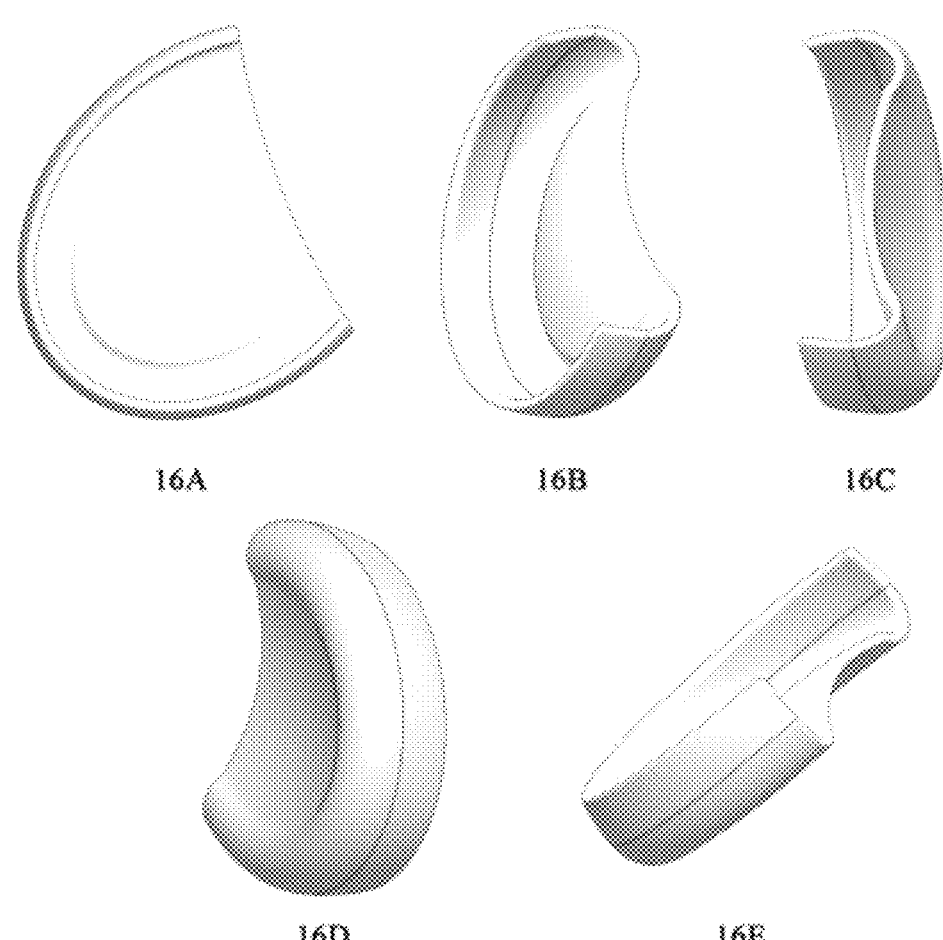
FIGS. 16A-16E show four perspectives of a prosthesis manufactured in accordance with the present invention.

As shown in FIGS. 12A-12C, the prosthesis is in a shape of circular arc and matches more than ⅛ of the edge the lower lung lobe. The section of the prosthesis is close to circular. The radius of the section is about 1.0 cm.

The prosthesis may be sewed onto the side wall of pleural cavity far from the heart. At the end of normal inspiratory, the prosthesis presses the lower part of the lung lobe and the mechanical tension of alveolar epithelium is reduced.

Example 13

As shown in FIGS. 13A-13D, the prosthesis is in a shape of plate and matches more than ⅓ area of the basal of the lower lung lobe. The lateral side has a height of about 1.0 cm. The prosthesis has a thickness of about 0.4 cm. The prosthesis has a concave bottom. The prosthesis may be sewed onto the side wall of pleural cavity. The sides of the prosthesis are round and smooth as far as possible.

At the end of normal inspiratory, the prosthesis presses the lower part of the lung lobe and the mechanical tension of alveolar epithelium is reduced.

Example 14

As shown in FIGS. 14A-14D, the prosthesis is in a shape of plate and matches more than ⅓ area of the basal of the lower lung lobe. The lateral side has a height of about 4 cm. The prosthesis has a thickness of about 1.0 cm. The prosthesis may be sewed onto the side wall of pleural cavity. The sides of the prosthesis are round and smooth as far as possible.

At the end of normal inspiratory, the prosthesis presses the lower part of the lung lobe and the mechanical tension of alveolar epithelium is reduced.

Example 15

As shown in FIGS. 15A-15D, the prosthesis is in a shape of half plate and matches more than ⅓ area of the basal of the lower lung lobe. The lateral side has a height of about 5 cm. The prosthesis has a thickness of about 0.5 cm. The prosthesis may be sewed onto the side wall of pleural cavity. The sides of the prosthesis are round and smooth as far as possible.

At the end of normal inspiratory, the prosthesis presses the lower part of the lung lobe and the mechanical tension of alveolar epithelium is reduced.

Example 16

As shown in FIGS. 16A-16E, the prosthesis is in a shape of half plate and matches more than ⅓ area of the basal of the lower lung lobe. The lateral side has a height of about 3 cm. The prosthesis has a thickness of about 0.3 cm. The prosthesis may be sewed onto the side wall of pleural cavity. The sides of the prosthesis are round and smooth as far as possible.

At the end of normal inspiratory, the prosthesis presses the lower part of the lung lobe and the mechanical tension of alveolar epithelium is reduced.

Example 17

Figure 17:
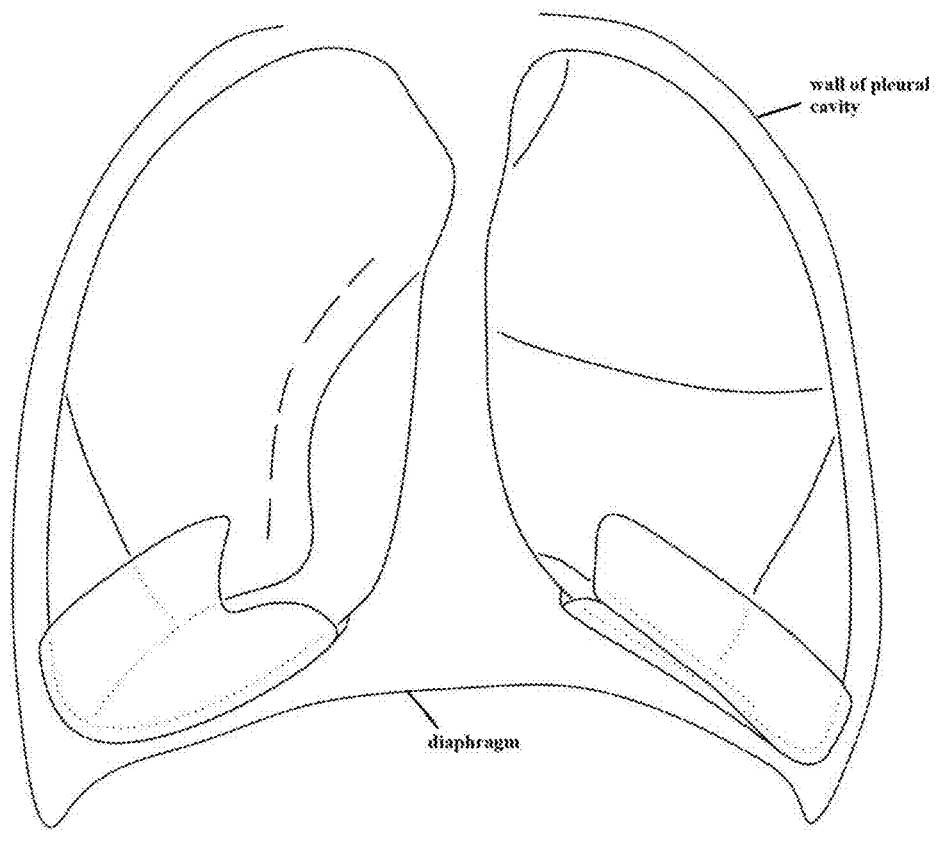
FIG. 17 illustrates a prosthesis of the present invention in position in a person's chest.

As shown in FIG. 17, a prosthesis of Example 4 is positioned in a persons's chest. At the end of normal inspiratory, the prosthesis presses the lower part of the lung lobe and the mechanical tension of alveolar epithelium is reduced.

Example 18

Generation and Characterization of Cdc42 AT2 Null Mice

In order to construct a progressive lung fibrosis animal model, Cdc42 AT2 null mice are generated by knocking out Cdc42 gene specifically in alveolar type II epithelial cells (AT2 cells).

Figure 18:
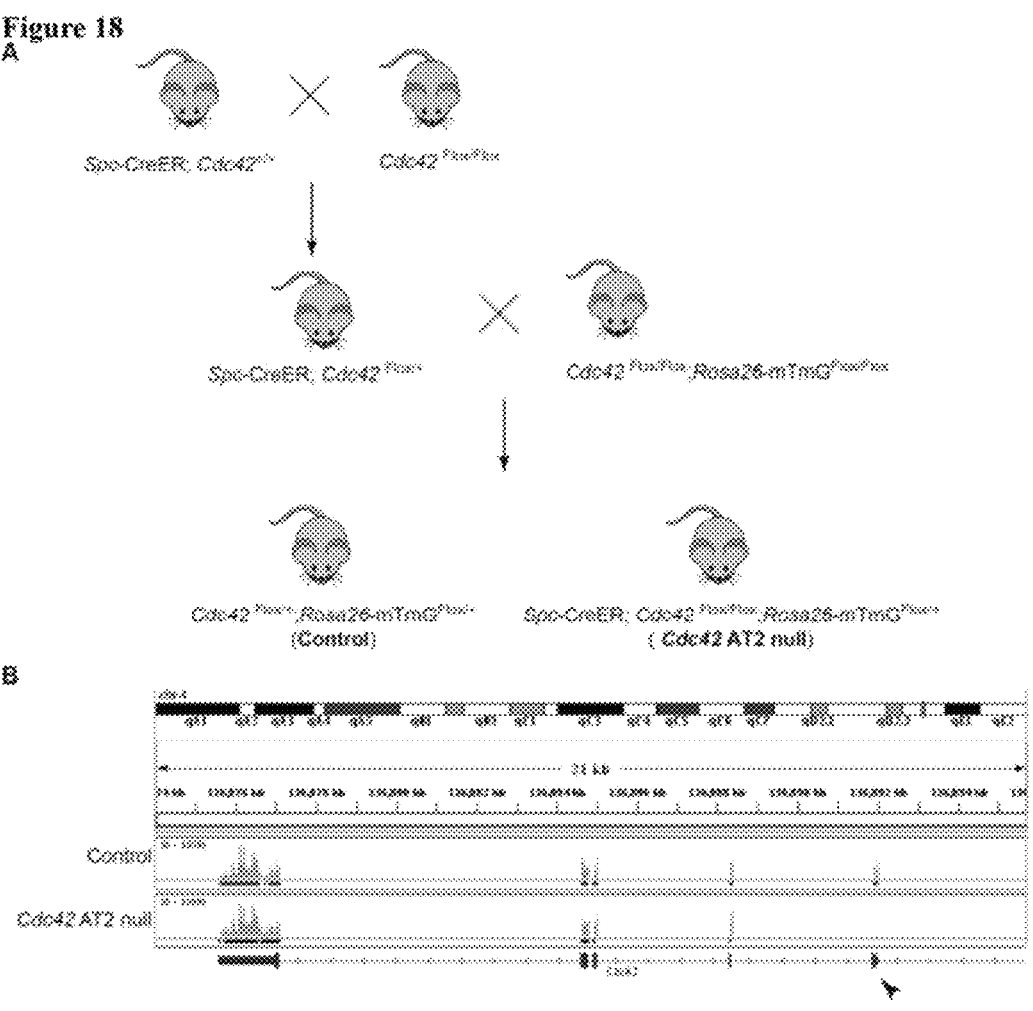
FIG. 18 shows that a mouse line in which Cdc42 gene is specifically deleted in AT2 cells is generated.

In order to specifically delete Cdc42 gene in AT2 cells, mice carrying a Spc-CreER knock-in allele are crossed with the Cdc42 floxed (Cdc42$^{flox/flox}$) mice (FIG. 18A). In Cdc42$^{flox/flox}$ mice, the exon 2 of Cdc42 gene, which contains the translation initiation exon of Cdc42 gene, is flanked by two loxp sites. In Spc-CreER; Cdc42$^{flox/flox}$ mice, the exon 2 of Cdc42 gene is specifically deleted in AT2 cells by Cre/loxp-mediated recombination after tamoxifen treatment (FIG. 18B). Spc-CreER; Cdc42$^{flox/flox}$ mice are named as Cdc42 AT2 null mice.

The Spc-CreER, Cdc42$^{flox/-}$ mice were performed genome purification and PCR amplification. Then the fox and null bands of Cdc42 were purified and sequenced using the primers as below: CTGCCAACCATGACAACCTAA (SEQ ID NO:23);

(SEQ ID NO: 24)
AGACAAAACAACAAGGTCCAG.

The fragments of Cdc42 DNA sequence before or after deleting the exon2 of the Cdc42 gene are shown in FIG. 25.

Figure 19:
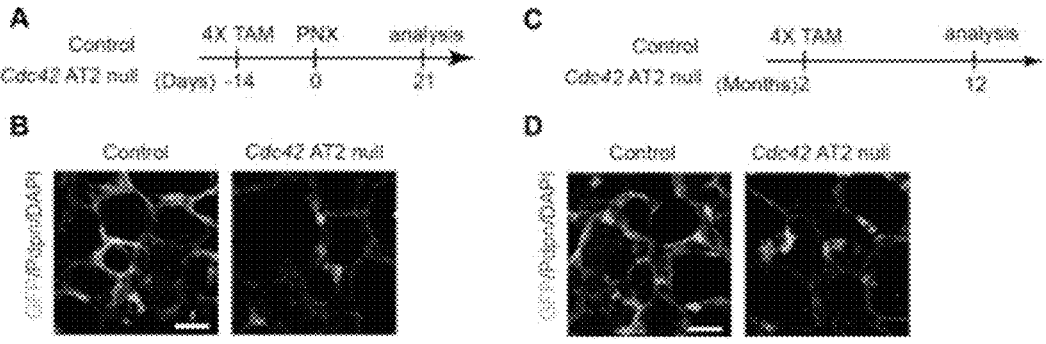
FIG. 19 shows that loss of Cdc42 gene in AT2 cells impairs the differentiation of AT2 cells during post-PNX alveolar regeneration or alveolar homeostasis.

As shown in (FIG. 19A), 200 μm lung sections of Control and Cdc42 AT2 null mice are immunostained with antibodies against GFP, Pdpn, and Prospc. At post-PNX day 21, many newly differentiated AT1 cells and newly formed alveoli are observed in Control lungs (FIG. 19B). However, in Cdc42 AT2 null lungs, few AT2 cells have differentiated into AT1 cells, and no new alveoli are formed at post-PNX day 21 (FIG. 19B). It is observed that the alveoli in peripheral region of PNX-treated Cdc42 AT2 null lungs are profoundly overstretched (FIG. 19B).

During alveolar homeostasis, AT2 cells slowly differentiate into AT1 cells and build new alveoli. When 12-month Cdc42 AT2 null mice that had not undergone PNX are examined, enlarged alveoli with lacking any new AT1 cell formation are observed; and in contrast, the lungs of 12-month Control mice exhibit formation of many new alveoli (FIGS. 19C and 19D).

PNX-treated Cdc42 AT2 null and Control mice are observed for a longer period of time after PNX treatment (FIG. 20A). Some Cdc42 AT2 null mice show significant weight loss and increased respiration rates at post-PNX day 30. Indeed, fully 50% of PNX-treated Cdc42 AT2 null mice reach the predefined health-status criteria for endpoint euthanization by post-PNX day 60 (FIG. 20B), and about 80% of PNX-treated Cdc42 AT2 null mice reach their endpoints by post-PNX day 180 (FIG. 20B).

H&E staining of PNX-treated Control and Cdc42 AT2 null mice reveals severe fibrosis in the lungs of Cdc42 AT2 null mice at their endpoints (FIGS. 20C-20D). In order to determine the point at which Cdc42 AT2 null mice begin to develop lung fibrosis following PNX, the lungs of Cdc42 AT2 null mice are analyzed at various time points after PNX using H&E staining (FIG. 20D). The subpleural regions of some Cdc42 AT2 null lungs exhibit signs of tissue thickening by post-PNX day 21 (FIG. 20D compared with control lung in FIG. 20C). By the end-point, the dense fibrosis has progressed to the centre of most Cdc42 AT2 null lungs.

In addition to detecting strong immunofluorescence signals for Collagen I in these dense fibrotic regions (FIG. 20E), we observe the proportion of Collagen I expressing area per lobe gradually increased in Cdc42 AT2 null mice after PNX (FIG. 20F). Our qPCR analysis also shows that the Collagen I mRNA expression levels increased gradually from post-PNX day 21 (FIG. 20G). Moreover, gradually decreased lung compliance is observed in PNX-treated Cdc42 AT2 null mice from post-PNX day 21 as compared to their PNX-treated Control mice (FIG. 20H), an intriguing finding given that decreased lung compliance is known to occur frequently as lungs become fibrotic[20-25].

Control and Cdc42 AT2 null mice were exposed to 4 doses of tamoxifen 14 days starting at age of 2 months. Lungs of Control and Cdc42 AT2 null mice without PNX treatment were collected at 10, 12, 16, or 24 months (FIG. 21A). The lungs of Control and Cdc42 AT2 null mice without PNX treatment were analyzed and found no significant fibrotic changes before the Cdc42 AT2 null mice reached 10-months of age (FIGS. 21B and 21C). By 12 months, fibrosis had obviously begun to develop in the subpleural regions of Cdc42 AT2 null lungs and to progress toward the center of the lung (FIG. 21C). Thus, the loss of Cdc42 in AT2 cells leads to progressive lung fibrosis in no-PNX-treated Cdc42 AT2 null mice starting from around 12 months of age.

Fibroblastic foci are considered a relevant morphologic marker of progressive pulmonary fibrosis and are recognized as sites where fibrotic responses are initiated and/or perpetuated in progressive pulmonary fibrosis. The fibroblastic foci contain proliferating α-SMA⁺ fibroblasts. Lungs of Cdc42 AT2 null mice at post-PNX day 21 are stained with antibodies against α-SMA (FIG. 22A). Some α-SMA⁺ fibroblasts accumulating next to a cluster of AT2 cells (GFP⁺ cells) in the relative normal alveolar regions of Cdc42 AT2 null lungs are observed (area 1, FIG. 22A). And the dense fibrosis region of the lungs is filled with α-SMA⁺ fibroblasts (area 2, FIG. 22A). In addition, the cell proliferation of α-SMA⁺ cells is increased dramatically in the lungs of Cdc42 AT2 null mice at post-PNX day 21 by immunostaining using antibodies against both α-SMA and proliferation marker, Ki67, indicating that the proliferating α-SMA⁺ fibroblasts contribute to the development of lung fibrosis (FIG. 22B).

Example 19

Elevated Mechanical Tension Caused by Impaired Alveolar Regeneration Leads to Progressive Lung Fibrosis The fact that lung fibrosis in Cdc42 AT2 null mice is greatly accelerated by the PNX treatment (FIG. 20) suggests a close link between lung fibrosis and mechanical tension-induced alveolar regeneration.

The loss of alveoli resulting from PNX substantially increases mechanical tension exerted upon the alveolar epithelium. The subsequent efficient regeneration of alveoli that occurs in normal mice eventually reduces the intensity of the mechanical tension to pre-PNX levels; however, as Cdc42 null AT2 cells are unable to differentiate into AT1 cells and thus cannot regenerate new alveoli (FIG. 19B), the alveolar epithelium of Cdc42 AT2 null mice continue to experience elevated mechanical tension (FIG. 19B), which results in the progressive development of fibrosis (FIG. 20D).

Example 20

Progressive Lung Fibrosis Can be Prevented by the Prosthesis Implantation

Figure 23:
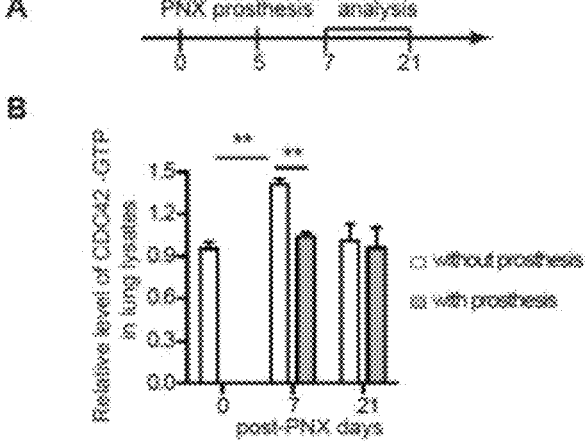
FIG. 23 shows that the expression level of CDC42-GTP increases significantly at post-PNX day 7.

By measuring the expression levels of CDC42-GTP, the GTP-bound state of CDC42, in the post-PNX lungs, it is found that the activity of CDC42-GTP increased significantly at post-PNX day 7 (FIG. 23A-23B). Such increased expression of CDC42-GTP can be inhibited by implanting a prosthesis in the chest (FIGS. 23A-23B).

Figure 24:
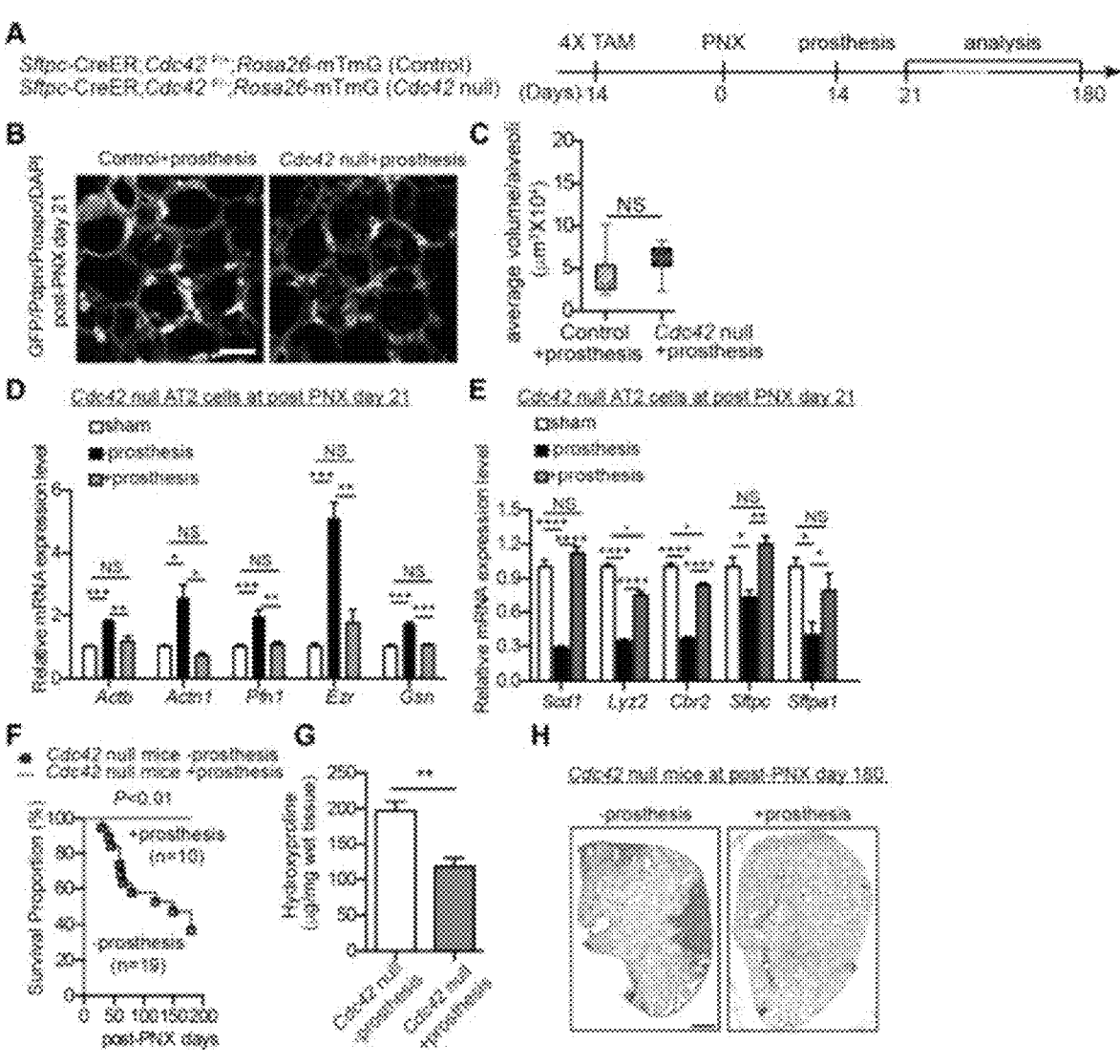
FIG. 24 shows that reducing mechanical tension on alveoli attenuates progressive lung fibrosis.

As shown in FIGS. 24A-24H, reducing mechanical tension on alveoli attenuate progressive lung fibrosis. Control and Cdc42 AT2 null mice were exposed to 4 doses of tamoxifen 14 days prior to PNX. A prosthesis was implanted at post-PNX day 14 (FIG. 24A). Lungs of prosthesis-implanted Control and Cdc42 AT2 null mice were collected at post-PNX day 21. Images show the maximum intensity of a 200 μm Z-projection of lung sections that were stained with antibodies against GFP, Pdpn, and Prospc (FIG. 24B). The average alveolar size of prosthesis-implanted Control and Cdc42 AT2 null mice is not significantly different at post-PNX day 21 (mean±S.E.M., n=3), indicating the enlarged alveoli phenotype of Cdc42 AT2 null lungs can be greatly rescued by the implantation of the prosthesis (FIGS. 24B-24C). Recalling moderately increased actin-cytoskeleton regulatory genes and decreased expression levels of surfactant-associate genes were observed in IPF patient lungs. By qPCR, we compared the expression levels of actin-cytoskeleton regulatory genes and AT2 biomarker genes in AT2 cells of non-prosthesis and prosthesis implanted Cdc42 AT2 null mice (mean±S.E.M., n=3). In non-prosthesis implanted Cdc42 null AT2 cells, the expression levels of actin-cytoskeleton regulatory genes are increased and the expression levels of AT2 biomarker genes are decreased (FIGS. 24D-24E). The prosthetic implantation not only suppressed the increased expression of actin-cytoskeleton regulatory genes (FIG. 24D), but also greatly rescued the decreased expression of AT2 biomarker genes (FIG. 24E). Our results support the conclusion that the increased mechanical tension in the overstretched alveoli of Cdc42 AT2 null lungs positively regulates actin-cytoskeleton regulatory genes and negatively regulates the expression of AT2 biomarker genes. The percentage of survivors among the no-prosthesis-implanted and prosthesis-implanted Cdc42 AT2 null mice were calculated at post-PNX day 180. Strikingly, by post-PNX 180 days, none of the Cdc42 AT2 null mice (n=10) that were implanted with a prosthesis died while fully 70% of the no-prosthesis-implanted Cdc42 AT2 null mice (n=19) were dead by this time point (FIG. 24F). The levels of hydroxyproline in the lungs of no-prosthesis-implanted and prosthesis-implanted Cdc42 AT2 null mice when no-prosthesis-implanted Cdc42 AT2 null mice reached their end points (mean±S.E.M., n=5) (FIG. 24G). H&E staining revealed that little to no lung fibrosis was evident in prosthesis-implanted Cdc42 AT2 null mice by post-PNX day 180, whereas modest to severe lung fibrosis was observed in all of the surviving Cdc42 AT2 null mice that were not given a prosthesis following PNX (FIG. 24H). Together, these results demonstrate an essential regulatory role for the mechanical tension in driving the development of lung fibrosis in Cdc42 AT2 null mice. *P<0.05, P<0.01, *P<0.001; ****P<0.0001, NS, not significant, Student's t test. Scale bar: 20 µm (B); 2 mm (H).

Figure 20:
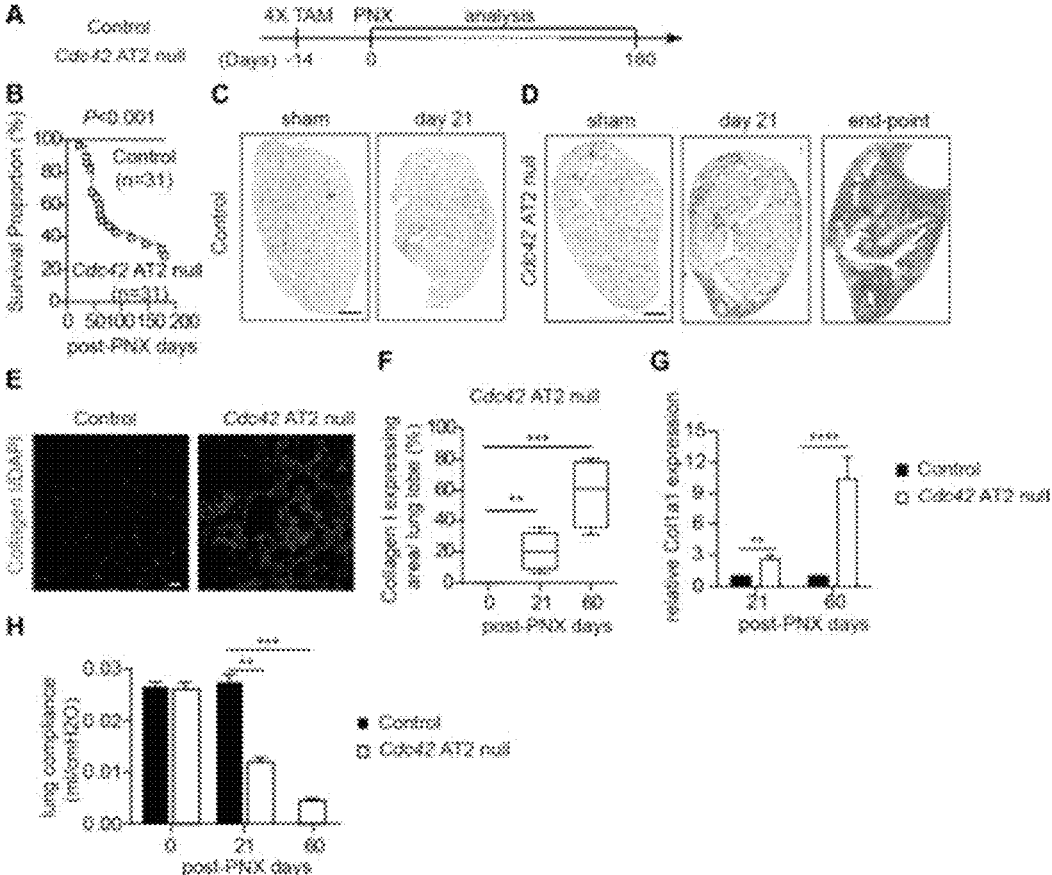
FIG. 20 shows that loss of Cdc42 gene in AT2 cells leads to progressive lung fibrosis in PNX-treated mice.
Figure 21:
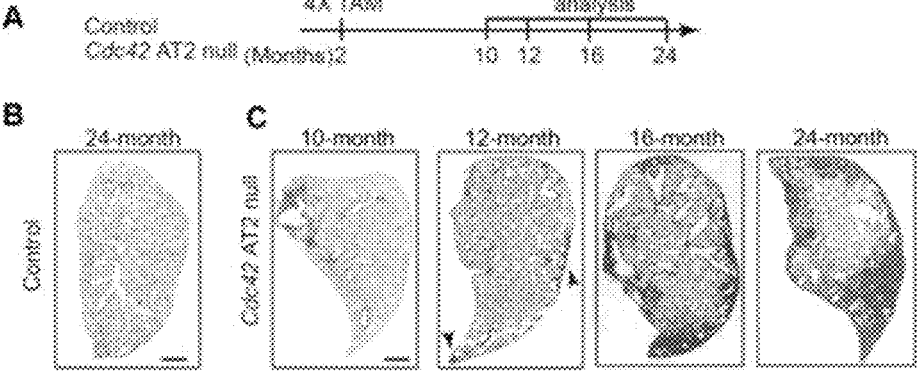
FIG. 21 shows that loss of Cdc42 gene in AT2 cells leads to progressive lung fibrosis in non-PNX-treated aged mice.
Figure 22:
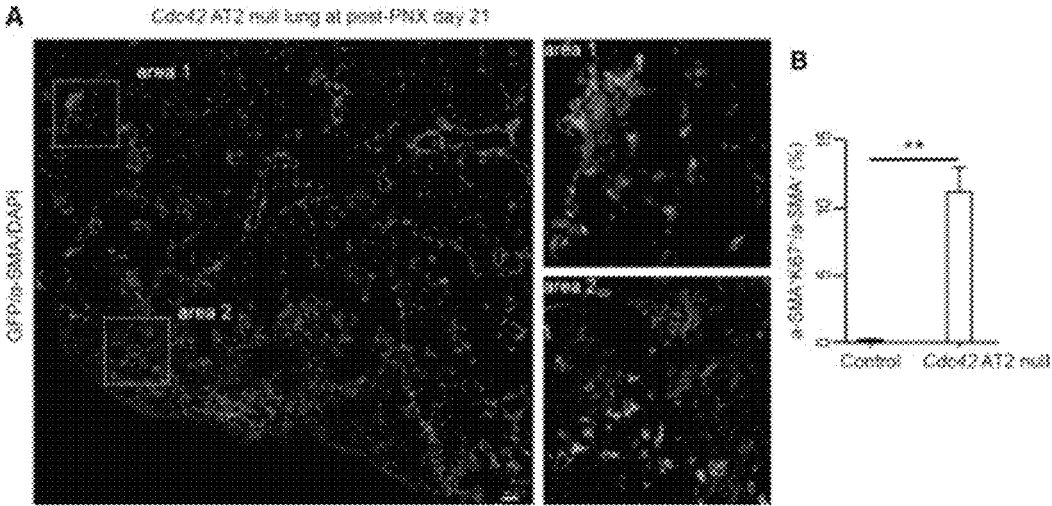
FIG. 22 shows the development of $\alpha$-SMA$^+$ fibroblastic foci in the lungs of Cdc42 AT2 null mice.

As shown in FIG. 20-FIG. 22, the loss of Cdc42 in AT2 cells leads to progressive lung fibrosis following lung injury. The progressive development of lung fibrosis that we observed here is apparently similar to the pathological process that occurs in IPF patients, in which fibrosis initially starts at peripheral regions of the lung before slowly proceeding inwards, eventually affecting entire lung lobes. We show that the loss of alveoli resulting from PNX substantially increases mechanical tension exerted upon the alveolar epithelium. The subsequent efficient regeneration of alveoli that occurs in normal mice eventually reduces the intensity of the mechanical tension to pre-PNX levels; however, as Cdc42 null AT2 cells are unable to differentiate into AT1 cells and thus cannot regenerate new alveoli, the alveolar epithelium of Cdc42 null mice continue to experience elevated mechanical tension.

And further, the present invention provides a whole new and inventive method for treating IPF, the progression of which could not be reversed or even slowed down up to now. The present method uses pulmonary prosthesis implanted in the pleural cavity of human beings and is an efficient method for treating IPF without using any drugs.

REFERENCES

1 Wynn, T. Cellular and molecular mechanisms of fibrosis. *The Journal of Pathology: A Journal of the Pathological Society of Great Britain and Ireland* 214, 199-210 (2008).

2 Wynn, T. A. & Ramalingam, T. R. Mechanisms of fibrosis: therapeutic translation for fibrotic disease. *Nature medicine* 18, 1028 (2012).

3 Mehal, W. Z., Iredale, J. & Friedman, S. L. Scraping fibrosis: expressway to the core of fibrosis. *Nature medicine* 17, 552 (2011).

4 Barkauskas, C. E. & Noble, P. W. Cellular mechanisms of tissue fibrosis. 7. New insights into the cellular mechanisms of pulmonary fibrosis. *American Journal of Physiology-Cell Physiology* 306, C987-C996 (2014).

5 Rock, J. R. et al. Multiple stromal populations contribute to pulmonary fibrosis without evidence for epithelial to mesenchymal transition. *Proceedings of the National Academy of Sciences* 108, E1475-E1483 (2011).

6 Gross, T. J. & Hunninghake, G. W. Idiopathic pulmonary fibrosis. *New England Journal of Medicine* 345, 517-525 (2001).

7 Vyalov, S. L., Gabbiani, G. & Kapanci, Y. Rat alveolar myofibroblasts acquire alpha-smooth muscle actin expression during bleomycin-induced pulmonary fibrosis. *The American journal of pathology* 143, 1754 (1993).

8 King Jr, T. E., Pardo, A. & Selman, M. Idiopathic pulmonary fibrosis. *The Lancet* 378, 1949-1961 (2011).

9 Plantier, L. et al. Ectopic respiratory epithelial cell differentiation in bronchiolised distal airspaces in idiopathic pulmonary fibrosis. *Thorax* 66, 651-657 (2011).

10 Steele, M. P. & Schwartz, D. A. Molecular mechanisms in progressive idiopathic pulmonary fibrosis. *Annual review of medicine* 64, 265-276 (2013).

11 Nogee, L. M. et al. A mutation in the surfactant protein C gene associated with familial interstitial lung disease. *New England Journal of Medicine* 344, 573-579 (2001).

12 Seibold, M. A. et al. A common MUC5B promoter polymorphism and pulmonary fibrosis. *New England Journal of Medicine* 364, 1503-1512 (2011).

13 Wang, Y. et al. Genetic defects in surfactant protein A2 are associated with pulmonary fibrosis and lung cancer. *The American Journal of Human Genetics* 84, 52-59 (2009).

14 Barkauskas, C. E. et al. Type 2 alveolar cells are stem cells in adult lung. *The Journal of clinical investigation* 123, 3025-3036 (2013).

15 Desai, T. J., Brownfield, D. G. & Krasnow, M. A. Alveolar progenitor and stem cells in lung development, renewal and cancer. *Nature* 507, 190 (2014).

16 Haies, D. M., Gil, J. & Weibel, E. R. Morphometric study of rat lung cells: I. Numerical and dimensional characteristics of parenchymal cell population. *American Review of Respiratory Disease* 123, 533-541 (1981).

17 Selman, M. & Pardo, A. Idiopathic pulmonary fibrosis: an epithelial/fibroblastic cross-talk disorder. *Respiratory research* 3, 3 (2001).

18 Kropski, J. A., Blackwell, T. S. & Loyd, J. E. The genetic basis of idiopathic pulmonary fibrosis. *European Respiratory Journal* 45, 1717-1727 (2015).

19 Goodwin, A. T. & Jenkins, G. Molecular endotyping of pulmonary fibrosis. *Chest* 149, 228-237 (2016).

20 Meltzer, E. B. & Noble, P. W. Idiopathic pulmonary fibrosis. *Orphanet journal of rare diseases* 3, 8, doi: 10.1186/1750-1172-3-8 (2008).

21 Richeldi, L., Collard, H. R. & Jones, M. G. Idiopathic pulmonary fibrosis. *The Lancet* 389, 1941-1952, doi: 10.1016/s0140-6736(17)30866-8 (2017).

22 T E, J. K. et al. Idiopathic pulmonary fibrosis. *American journal of respiratory and critical care medicine* 161, 646-664 (2000).

23 Lynch, D. A. et al. High-resolution computed tomography in idiopathic pulmonary fibrosis: diagnosis and prognosis. *American journal of respiratory and critical care medicine* 172, 488-493 (2005).

24 Noble, P. W. et al. Pirfenidone in patients with idiopathic pulmonary fibrosis (CAPACITY): two randomised trials. *The Lancet* 377, 1760-1769 (2011).

25 Raghu, G. et al. An official ATS/ERS/JRS/ALAT statement: idiopathic pulmonary fibrosis: evidence-based guidelines for diagnosis and management. *American journal of respiratory and critical care medicine* 183, 788-824 (2011).

---

The invention claimed is:

1. A method for treating pulmonary fibrosis, comprising following steps: reducing mechanical tension on the alveolar epithelium at an end of normal inspiratory, by placing a prosthesis under a pulmonary lobe of a lung in the pleural cavity of a subject so as to reduce the level of mechanical tension on the alveolar epithelium at the end of normal inspiratory, wherein the subject has pulmonary fibrosis in the lung; and attenuating progression of the pulmonary fibrosis of the subject, wherein the prosthesis is in a shape of plate, ellipse, irregular U, arc, conical, scapula, or irregular, so as to occupy the space under the lung lobe, wherein the prosthesis is solid, wherein the prosthesis is made of soft spongy latex, foam latex, 380 micron hollow fiber, gelatin foam, plastic sponge, rubber, silicone rubber, silicone gel, carbon nanotube, graphene, ultra-light porous carbon, hollow porous carbon, carbon fiber, or carbon titanium alloy, wherein the prosthesis occupies at least ¼ of a space surrounded by a basal area of the pulmonary lobe, diaphragm and a wall of pleural cavity at the end of normal inspiratory, wherein the prosthesis comprises a body having an upper side, a lower side, a lateral side extending between the upper side and the lower side, and a medial border approaching the heart, wherein the lateral side is opposite to the medial border, and wherein the lateral side is at a height of 0.5 cm-8 cm, and thickness of a wall of the prosthesis is between 0.1-4 cm.

2. The method of claim 1, wherein the prosthesis is fixed in the pleural cavity, and the prosthesis is placed at the lower part of the pleural cavity.

3. The method of claim 1, wherein the prosthesis is sutured to the wall of pleural cavity, or to the lower part of the wall of the pleural cavity.

4. The method of claim 1, wherein the prosthesis is designed to be anchored under the lobes and above the diaphragm, and is designed to be matched with the basal of the lobes, as long as the level of mechanical tension on the alveolar epithelium is reduced at the end of normal inspiratory.

5. The method of claim 1, wherein the prosthesis is surrounded by pleural fluid.

6. The method of claim 1, wherein the area of the prosthesis projected to the bottom of the lower lung lobe accounts for at least half, at least ¾, or the whole of the area of the bottom of the lower lung lobe.

7. The method of claim 1, wherein the upper side of the body of the prosthesis is matched with the bottom of the lobes, wherein the lower side of the body of the prosthesis is matched with the diaphragm, wherein an outer lateral side of the prosthesis is matched with a wall of pleural cavity between a bottom of the lobes and the diaphragm far from a heart, and/or wherein an inner lateral side of the prosthesis is matched with an outer wall of a lower lung lobe.

8. The method of claim 1, wherein the prosthesis has a smooth curved profile without edges and corners so as to reduce the discomfort and avoid injury to the pleura.

9. The method of claim 1, wherein the prosthesis upper side tapers toward the medial border, and the prosthesis lower side tapers toward the medial border.

10. The method of claim 1, wherein the prosthesis is in a shape of arc, and the arc is matched with the lower edge of the lower lung lobe.

11. The method of claim 10, wherein the arch is matched with or at least ½ of the lower edge of the lower lung lobe far from a heart.

12. The method of claim 1, wherein the prosthesis is at a height of 1 cm-4 cm.

13. The prosthesis of claim 3, wherein the prosthesis is sutured to the pleural cavity wall or to the lower part of the pleural cavity wall, using surgical sutures.

14. The prosthesis of claim 3, wherein the prosthesis is sutured to of the wall of pleural cavity through pinholes on the lateral side.

15. The prosthesis of claim 1, wherein the pulmonary fibrosis is idiopathic pulmonary fibrosis.

16. The prosthesis of claim 10, wherein the arch is matched with the overall length of the lower edge of the lower lung lobe.

* * * * *

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Synthetic forward primer for Gapdh

<400> SEQUENCE: 1
aaggtcggtg tgaacggatt tgg                                                      23

<210> SEQ ID NO 2
<211> LENGTH: 23
<212> TYPE: DNA
<213> ORGANISM: Artificial Sequence
<220> FEATURE:
<223> OTHER INFORMATION: Synthetic reverse primer for Gapdh

<400> SEQUENCE: 2
cgttgaattt gccgtgagtg gag                                                      23

<210> SEQ ID NO 3
<211> LENGTH: 20
<212> TYPE: DNA
<213> ORGANISM: Artificial Sequence
<220> FEATURE:
<223> OTHER INFORMATION: Synthetic forward primer for Sftpc

<400> SEQUENCE: 3
ttgtcgtggt gattgtaggg                                                         20

<210> SEQ ID NO 4
<211> LENGTH: 20
<212> TYPE: DNA
<213> ORGANISM: Artificial Sequence
<220> FEATURE:
<223> OTHER INFORMATION: Synthetic reverse primer for Sftpc

<400> SEQUENCE: 4
tggaaaaggt agcgatggtg                                                         20

<210> SEQ ID NO 5
<211> LENGTH: 22
<212> TYPE: DNA
<213> ORGANISM: Artificial Sequence
<220> FEATURE:
<223> OTHER INFORMATION: Synthetic forward primer for Scd1

<400> SEQUENCE: 5
gcaagctcta cacctgcctc tt                                                       22

<210> SEQ ID NO 6
<211> LENGTH: 22
<212> TYPE: DNA
<213> ORGANISM: Artificial Sequence
<220> FEATURE:
<223> OTHER INFORMATION: Synthetic reverse primer for Scd1

<400> SEQUENCE: 6
cgtgccttgt aagttctgtg gc                                                       22

```
<210> SEQ ID NO 7
<211> LENGTH: 24
<212> TYPE: DNA
<213> ORGANISM: Artificial Sequence
<220> FEATURE:
<223> OTHER INFORMATION: Synthetic forward primer for Lyz2

<400> SEQUENCE: 7
tgccagaact ctgaaaagga atgg                                              24

<210> SEQ ID NO 8
<211> LENGTH: 22
<212> TYPE: DNA
<213> ORGANISM: Artificial Sequence
<220> FEATURE:
<223> OTHER INFORMATION: Synthetic reverse primer for Lyz2

<400> SEQUENCE: 8
cagtgctttg gtctccacgg tt                                                22

<210> SEQ ID NO 9
<211> LENGTH: 23
<212> TYPE: DNA
<213> ORGANISM: Artificial Sequence
<220> FEATURE:
<223> OTHER INFORMATION: Synthetic forward primer for Cbr2

<400> SEQUENCE: 9
catgggcaag aaagtctctg cag                                               23

<210> SEQ ID NO 10
<211> LENGTH: 22
<212> TYPE: DNA
<213> ORGANISM: Artificial Sequence
<220> FEATURE:
<223> OTHER INFORMATION: Synthetic reverse primer for Cbr2

<400> SEQUENCE: 10
actggtagag gcacttctgt cg                                                22

<210> SEQ ID NO 11
<211> LENGTH: 22
<212> TYPE: DNA
<213> ORGANISM: Artificial Sequence
<220> FEATURE:
<223> OTHER INFORMATION: Synthetic forward primer for Sftpa1

<400> SEQUENCE: 11
acctggatga ggagcttcag ac                                                22

<210> SEQ ID NO 12
<211> LENGTH: 23
<212> TYPE: DNA
<213> ORGANISM: Artificial Sequence
<220> FEATURE:
<223> OTHER INFORMATION: Synthetic reverse primer for Sftpa1

<400> SEQUENCE: 12
ctgactgccc attggtggaa aag                                               23

<210> SEQ ID NO 13
<211> LENGTH: 23
<212> TYPE: DNA
<213> ORGANISM: Artificial Sequence
<220> FEATURE:
<223> OTHER INFORMATION: Synthetic forward primer for Actb
```

-continued

<400> SEQUENCE: 13
cattgctgac aggatgcaga agg                                              23

<210> SEQ ID NO 14
<211> LENGTH: 22
<212> TYPE: DNA
<213> ORGANISM: Artificial Sequence
<220> FEATURE:
<223> OTHER INFORMATION: Synthetic reverse primer for Actb

<400> SEQUENCE: 14
tgctggaagg tggacagtga gg                                               22

<210> SEQ ID NO 15
<211> LENGTH: 22
<212> TYPE: DNA
<213> ORGANISM: Artificial Sequence
<220> FEATURE:
<223> OTHER INFORMATION: Synthetic forward primer for Actn1

<400> SEQUENCE: 15
tcgccaagtg tcaacgctcg tt                                               22

<210> SEQ ID NO 16
<211> LENGTH: 22
<212> TYPE: DNA
<213> ORGANISM: Artificial Sequence
<220> FEATURE:
<223> OTHER INFORMATION: Synthetic reverse primer for Actn1

<400> SEQUENCE: 16
ggtcgatggt ttccagcagc tt                                               22

<210> SEQ ID NO 17
<211> LENGTH: 22
<212> TYPE: DNA
<213> ORGANISM: Artificial Sequence
<220> FEATURE:
<223> OTHER INFORMATION: Synthetic forward primer for Pfn1

<400> SEQUENCE: 17
catcgtaggc tacaaggact cg                                               22

<210> SEQ ID NO 18
<211> LENGTH: 22
<212> TYPE: DNA
<213> ORGANISM: Artificial Sequence
<220> FEATURE:
<223> OTHER INFORMATION: Synthetic reverse primer for Pfn1

<400> SEQUENCE: 18
ccaagtgtca gcccattgac ga                                               22

<210> SEQ ID NO 19
<211> LENGTH: 22
<212> TYPE: DNA
<213> ORGANISM: Artificial Sequence
<220> FEATURE:
<223> OTHER INFORMATION: Synthetic forward primer for Ezr

<400> SEQUENCE: 19
atcgaggtgc agcagatgaa gg                                               22

<210> SEQ ID NO 20

-continued

```
<211> LENGTH: 22
<212> TYPE: DNA
<213> ORGANISM: Artificial Sequence
<220> FEATURE:
<223> OTHER INFORMATION: Synthetic reverse primer for Ezr

<400> SEQUENCE: 20
cggagcatct gctccttttc tc                                           22

<210> SEQ ID NO 21
<211> LENGTH: 22
<212> TYPE: DNA
<213> ORGANISM: Artificial Sequence
<220> FEATURE:
<223> OTHER INFORMATION: Synthetic forward primer for Gsn

<400> SEQUENCE: 21
ggctttgagt cgtccacctt ct                                           22

<210> SEQ ID NO 22
<211> LENGTH: 22
<212> TYPE: DNA
<213> ORGANISM: Artificial Sequence
<220> FEATURE:
<223> OTHER INFORMATION: Synthetic reverse primer for Gsn

<400> SEQUENCE: 22
gtcctttgac ctggaagagc ct                                           22

<210> SEQ ID NO 23
<211> LENGTH: 21
<212> TYPE: DNA
<213> ORGANISM: Artificial Sequence
<220> FEATURE:
<223> OTHER INFORMATION: Synthetic forward primer for Cdc42

<400> SEQUENCE: 23
ctgccaacca tgacaaccta a                                            21

<210> SEQ ID NO 24
<211> LENGTH: 21
<212> TYPE: DNA
<213> ORGANISM: Artificial Sequence
<220> FEATURE:
<223> OTHER INFORMATION: Synthetic reverse primer for Cdc42

<400> SEQUENCE: 24
agacaaaaca acaaggtcca g                                            21

<210> SEQ ID NO 25
<211> LENGTH: 1128
<212> TYPE: DNA
<213> ORGANISM: Mus musculus

<400> SEQUENCE: 25
tgttctattt taaagtacag gtaatcatgc atgagaagtc aaaaccttta aaactgtcaa    60
acagtgggct gctgtgtgtg gcatttgctg ccaaccatga caacctaagt tcaacttaag   120
agcccaacaa tggaaaaaga cccccttcaag ttgtcctctg ccatctacac atacaccaaa   180
gcaggacaca ggtatgtaca gaattcataa cttcgtataa tgtatgctat acgaagttat   240
gttcgaacga agttcctatt ctctagaaag tataggaact tcgctagact agtacgcgtg   300
tacaccttgt aattgctgct ctgagcaagt tgccattttt tcttttttaga ggttttcagt   360 catagcagta atgctagttc tggtttgagt ggctgagcct gttgctaggg gaaaaaagta   420
```

-continued

```
tggatttaaa cataaatcaa taaaataatt gtctttaatt tcttcttagg acaagatcta      480
atttgaaata ttaaaagtgg atacaaaact gtttccgaaa tgcagacaat taagtgtgtt      540
gttgttggtg atggtgctgt tggtaaaaca tgtctcctga tatcctacac aacaaacaaa      600
ttcccatcgg aatatgtacc aactgtaagt ataaaggctt tttactagca aaagattgta      660
atgtagtgtc tgtccattgg aaaacacttg gcctgcctgc agtatttttg actgtcttgc      720
cctttaaaaa aaattaaatt ttactacctt tattactttg tggggtgtgt gttataactt      780
cgtataatgt atgctatacg aagttatggt accgaattca gtttctggac cttgttgttt      840
tgtcttaagt atcaaagtag aacagtgacc gatatattcc tttattttt ttttttcttc      900 cctgagactg ggtttctctg tgtagccctt gctgttctgt aactcactct gtgagtggcc      960
tcaaactcag agatccgcct gccttgggca aggaaggtgc tataaaaga gtctcgtgtg     1020 gtatatgaag tatagtttgt gaaagctgct tcagtgtgag cacacacgca ttatatgcaa     1080
gaccaattgc agcccgaaga atactctaaa aaatgactca ctgcccag              1128
```

<210> SEQ ID NO 26
<211> LENGTH: 561
<212> TYPE: DNA
<213> ORGANISM: Mus musculus

<400> SEQUENCE: 26

```
tgttctattt taaagtacag gtaatcatgc atgagaagtc aaaacctta aaactgtcaa       60 acagtgggct gctgtgtgtg gcatttgctg ccaaccatga caacctaagt tcaacttaag      120
agcccaacaa tggaaaaaga ccccttcaag ttgtcctctg ccatctacac atacaccaaa      180
gcaggacaca ggtatgtaca gaattcataa cttcgtataa tgtatgctat acgaagttat      240
ggtaccgaat tcagtttctg gaccttgttg ttttgtctta agtatcaaag tagaacagtg      300
accgatatat tccttttatt tttttttttc ttccctgaga ctgggtttct ctgtgtagcc      360
cttgctgttc tgtaactcac tctgtgagtg gcctcaaact cagagatccg cctgccttgg      420
gcaaggaagg tgctataaaa agagtctcgt gtggtatatg aagtatagtt tgtgaaagct      480
gcttcagtgt gagcacacac gcattatatg caagaccaat tgcagcccga agaatactct      540
aaaaaatgac tcactgccca g                                            561
```